(12) United States Patent
Xie et al.

(10) Patent No.: US 12,350,482 B2
(45) Date of Patent: Jul. 8, 2025

(54) IMPELLER AND VENTRICULAR ASSIST DEVICE

(71) Applicant: ANHUI TONGLING BIONICS TECHNOLOGY CO., LTD., Anhui (CN)

(72) Inventors: Zhengkai Xie, Hefei (CN); Zheng Gong, Hefei (CN); Huan Liu, Hefei (CN)

(73) Assignee: ANHUI TONGLING BIONICS TECHNOLOGY CO., LTD., Hefei (CN)

( * ) Notice: Subject to any disclaimer, the term of this patent is extended or adjusted under 35 U.S.C. 154(b) by 427 days.

(21) Appl. No.: 18/054,159

(22) Filed: Nov. 10, 2022

(65) Prior Publication Data

US 2023/0330410 A1 Oct. 19, 2023

(30) Foreign Application Priority Data

Apr. 19, 2022 (CN) .......................... 202210413767.1

(51) Int. Cl.
*A61M 60/226* (2021.01)
*A61M 60/178* (2021.01)
(Continued)

(52) U.S. Cl.
CPC ........ *A61M 60/226* (2021.01); *A61M 60/178* (2021.01); *A61M 60/515* (2021.01); *A61M 60/538* (2021.01)

(58) Field of Classification Search
CPC .. A61M 60/237; A61M 60/419; A61M 60/13; A61M 60/148; A61M 60/178; A61M 60/216; A61M 60/422; A61M 60/538; A61M 60/82; A61M 60/857; A61M 60/139; A61M 60/414; A61M 60/515; A61M 60/569; A61M 60/806; A61M 60/808; A61M 60/81; A61M 60/824; A61M 60/825; A61M 2205/0238; A61M 2205/0266; A61M 2205/32; A61M 2205/3365; A61M 2205/3507; A61M 2205/8206; A61M 2210/127; A61M 2230/04; A61M 60/17; A61M 60/221; A61M 60/226; A61M 60/232; A61M 60/31; A61M 60/33; A61M 60/408; A61M 60/416; A61M 60/562; A61M 60/585; A61M 60/804; A61M 60/812; A61M 60/818; A61M 60/829;
(Continued)

(56) References Cited

U.S. PATENT DOCUMENTS

2019/0351120 A1* 11/2019 Kushwaha .......... A61M 60/237

* cited by examiner

*Primary Examiner* — Jon Eric C Morales
(74) *Attorney, Agent, or Firm* — METIS IP LLC

(57) ABSTRACT

An impeller and a ventricular assist device are provided. The impeller comprises a hub and at least one blade fixed on an outer periphery of the hub; the hub comprises an inlet end and an outlet end; the blade comprises an action surface, an contour line of the action surface comprises an outer edge profile line away from the hub, an endpoint of the outer edge profile line close to the inlet end is a start point of the profile line, and an endpoint of the outer edge profile line close to the outlet end is an end point of the profile line; the outer edge profile line is a smooth space curve, and a curvature of the outer edge profile line along an axial direction of the hub gradually decreases from the start point of the profile line to the end point of the profile line.

18 Claims, 32 Drawing Sheets

(51) Int. Cl.
  *A61M 60/515* (2021.01)
  *A61M 60/538* (2021.01)
(58) Field of Classification Search
  CPC .............. A61M 60/833; A61M 60/861; A61M 60/873; A61M 60/88; A61F 2/82; A61F 2002/068; F04D 29/2222; F04D 29/041
  See application file for complete search history.

IMPELLER AND VENTRICULAR ASSIST DEVICE

CROSS REFERENCE TO RELATED APPLICATION

This application claims priority of Chinese Patent Application No. 202210413767.1, filed on Apr. 19, 2022, the entire contents of which are hereby incorporated by reference.

TECHNICAL FIELD

The disclosure relates to the technical field of medical devices, and in particular to an impeller and a ventricular assist device.

BACKGROUND

A percutaneous left ventricular assist device (PLVAD, hereinafter referred to as a catheter pump) is a miniaturized blood pumping device that can be introduced into the heart and can be configured to assist or replace natural heart function through circular pumping or continuous pumping of blood and provide hemodynamic support for cardiogenic shock and acute heart failure. The hemodynamic force of the catheter pump is generated from the high-speed rotation of the impeller, and the designed structure of the impeller has an important influence on the hydraulic performance and hemolytic performance of the catheter pump.

SUMMARY

One of the embodiments of the present disclosure provides an impeller, comprising a hub and at least one blade fixed on an outer periphery of the hub; the hub comprises an inlet end and an outlet end; the blade comprises an action surface, a contour line of the action surface comprises an outer edge profile line away from the hub, an endpoint of the outer edge profile line close to the inlet end is a start point of the profile line, and an endpoint of the outer edge profile line close to the outlet end is an end point of the profile line; the outer edge profile line is a smooth space curve, and a curvature of the outer edge profile line along an axial direction of the hub gradually decreases from the start point of the profile line to the end point of the profile line.

In some embodiments, a curvature change rate of the outer edge profile line along the axial direction of the hub gradually decreases from the start point of the profile line to the end point of the profile line.

In some embodiments, an inclined angle between a tangent line at the start point of the profile line and a tangential velocity at the start point of the profile line is an inlet inclined angle of the outer edge profile line; a resultant velocity of an axial velocity at the start point of the profile line and the tangential velocity at the start point of the profile line is a relative velocity at the start point of the profile line, and an inclined angle between the relative velocity at the start point of the profile line and the tangential velocity at the start point of the profile line is an inlet installation angle of the outer edge profile line; the inlet inclined angle is greater than the inlet installation angle.

In some embodiments, an angle difference between the inlet inclined angle and the inlet installation angle is less than or equal to 5°.

In some embodiments, the calculation formula of the inlet installation angle is as follows:

$$a_m = \arctan\frac{V_a}{V_t};$$

in the formula, $a_m$ is the inlet installation angle, $V_a$ is the axial velocity at the start point of the profile line, and $V_t$ is the tangential velocity at the start point of the profile line;

the calculation formula of the axial velocity at the start point of the profile line is as follows:

$$V_a = \frac{Q}{A} = \frac{4Q}{\pi D^2};$$

in the formula, Q is a preset flow rate, A is a cross-sectional area of a catheter hole for installing the impeller, and D is an inner diameter of the catheter;

the calculation formula of the tangential velocity at the start point of the profile line is as follows:

$$V_t = \omega\frac{D}{2};$$

in the formula, $\omega$ is a preset rotational velocity of the blade.

In some embodiments, the angle of the inlet inclined angle is 25°-35°.

In some embodiments, the outer edge profile line is a spiral curve with Gaussian curvature gradient, and the formula is as follows:

$$x = 0.7 + 1.2 * \sin\left(\pi\frac{z+2.14}{5}\right)$$

$$y = 1.85 - 3.7e^{-0.5\left(\frac{z-1.3}{1.3}\right)^2}$$

In some embodiments, an inclined angle between an axial plane where the start point of the profile line is located and an axial plane where the end point of the profile line is located is a blade deflection angle, and the angle of the blade deflection angle is 90°-150°.

In some embodiments, the contour line of the action surface further comprises an inlet edge line intersecting with the start point of the profile line; when the impeller is projected along an axial direction of the hub, an inclined angle between the inlet edge line and the axial direction of the start point of the profile line is a tangential forward sweep angle, and the angle of the tangential forward sweep angle is 2°-8°.

In some embodiments, the contour line of the action surface further comprises the inlet edge line intersecting with the start point of the profile line; when the impeller is projected along a radial direction of the hub, an inclined angle between the inlet edge line and a horizontal line is an axial forward sweep angle, and the angle of the axial forward sweep angle is 10°-26°.

In some embodiments, in the same radial cross-section of the impeller, the ratio of an outer diameter of the blade to the outer diameter of the hub is 1.25-3.25.

In some embodiments, the ratio of a length of the blade to the length of the hub is 0.86-0.87 along the axial direction of the hub.

In some embodiments, the impeller has standard parameters of the impeller and adjustment parameters of the impeller, and the adjustment parameters of the impeller are parameters used to adjust the standard parameters of the impeller.

In some embodiments, the adjustment parameters of the impeller comprise a first adjustment parameter of the impeller and a second adjustment parameter of the impeller; the first adjustment parameter of the impeller is determined based on the standard parameters of the impeller and customization requirements, and the second adjustment parameter of the impeller is determined based on the first adjustment parameter of the impeller and patient information.

In some embodiments, the customization requirements comprise one or more of a hydraulic performance requirement, a blood pumping performance requirement, and a hemolytic performance requirement.

In some embodiments, the first adjustment parameter of the impeller comprises a first adjustment parameter and/or a first adjustment function of the outer edge profile line.

In some embodiments, the patient information comprises one or more of the patient's basic information, implantation location and blood vessel diameter.

In some embodiments, the second adjustment parameter of the impeller comprises one or more of an outer diameter of the blade, a second adjustment parameter, and a second adjustment function of the outer edge profile line.

One of the embodiments of the present disclosure provides a ventricular assist device, comprising: a catheter and the aforementioned impeller arranged in the catheter.

BRIEF DESCRIPTION OF THE DRAWINGS

The present disclosure will be further described by way of exemplary embodiments, which will be described in detail with reference to the accompanying drawings. These embodiments are not limiting, and in these embodiments, the same numbers refer to the same structures.

DETAILED DESCRIPTION

Figure 1:
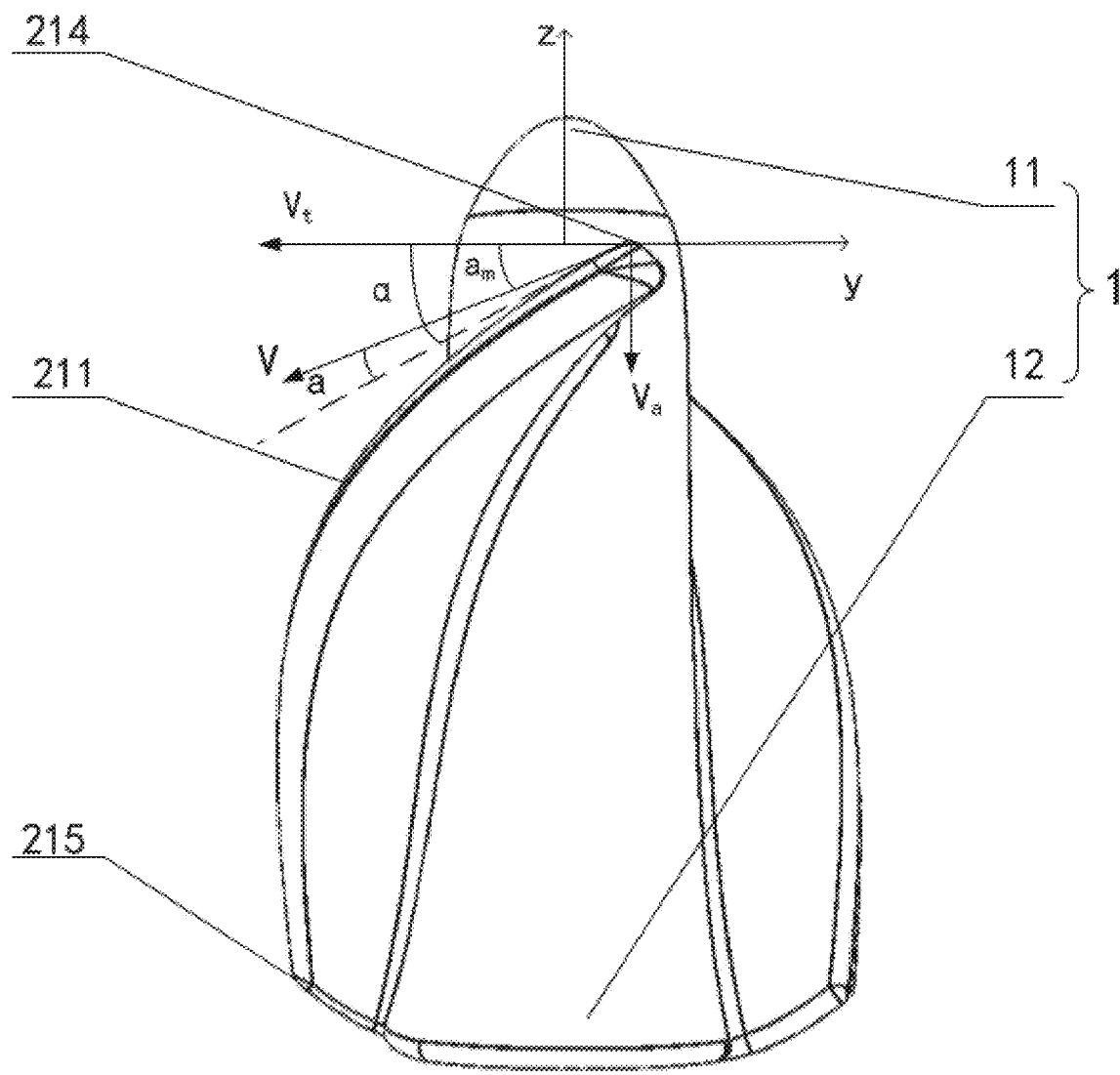
FIG. 1 is a front view of the impeller according to some embodiments of the present disclosure.

In order to illustrate the technical schemes of the embodiments of the present disclosure more clearly, the following briefly introduces the accompanying drawings used in the description of the embodiments. Obviously, the accompanying drawings in the following description are only some examples or embodiments of the present disclosure. For ordinary technicians skilled in the art, without creative efforts, the present disclosure can also be applied to other similar situations according to these accompanying drawings. Unless obvious from the locale or otherwise specified, the same reference numbers in the figures represent the same structure or operation.

It is to be understood that "system", "device", "unit" and/or "module" as used herein is a method used to distinguish different components, elements, parts, portions or assemblies at different levels. However, other words may be replaced by other expressions if they serve the same purpose.

As shown in the disclosure and claims, unless the context clearly dictates otherwise, the words "a", "an", and/or "the" are not intended to be specific in the singular form and may include the plural form. Generally speaking, the terms "comprising" and "including" only imply that the clearly identified steps and elements are included, these steps and elements do not constitute an exclusive list, and the method or equipment may also include other steps or elements.

Flowcharts are used in this disclosure to illustrate operations performed by the system according to the embodiment of this disclosure. It should be understood that the preceding or following operations are not necessarily performed in the exact order. Instead, the various steps may be processed in reverse order or simultaneously. At the same time, other operations may be added to these procedures, or a step or steps may be removed from these procedures.

The hydraulic performance and the hemolytic performance of the catheter pump are closely related to the structure of the impeller.

The hydraulic performance refers to a flow rate and a head that the catheter pump may achieve under the target volume and working conditions.

In order to enable the catheter pump to meet the blood circulation needs of different patients, there are various types of catheter pumps according to the blood output per minute, such as catheter pumps in 2.5 L/min-type, 3.5 L/min-type, and 5.0 L/min-type.

Hemolysis refers to the rupture of red blood cells in the blood, causing the hemoglobin in the red blood cells to overflow and dissolve in the blood. Hemolysis may lead to changes in the morphological and biochemical properties of red blood cells, shortened lifespan, or even complete rupture, thereby reducing the ability of red blood cells to deliver oxygen to tissues and organs. In addition, the plasma free hemoglobin concentration increases after hemolysis, and the excess free hemoglobin needs to be excreted by the kidneys, which may lead to renal damage and multiple uterine failure. Therefore, when blood is pumped to a medical subject, it is very important to prevent hemolysis of the pumped blood. If the blood is hemolyzed during pumping, it will endanger the life of the medical subject.

In order to ensure the safe use of the catheter pump, it is necessary to consider the hemolytic performance. The so-called hemolytic performance refers to the probability of hemolysis due to the damage of blood cells after the blood flows through the catheter pump.

In order to meet the requirements of the hydraulic performance and the hemolytic performance, the impeller may adopt a micro-axial flow structure.

In order to reduce the impact of the implantation operation on the normal physiology of the human body, the outer diameter of the impeller is usually limited to be within 7 mm suitable for passing through the blood vessel, which makes the volume of the impeller and the blades on the impeller strictly limited, and then makes the hydraulic performance that the impeller can achieve is difficult to meet the standard. In order to meet the pressure value required by human blood circulation, it is necessary to increase the velocity of the impeller to improve the blood pumping performance, but the high-velocity rotation of the impeller will increase the shear stress of the blood flow field, resulting in the fragmentation of blood cells, and then mechanical hemolysis occurs.

Therefore, the structure of impeller for the catheter pump needs to consider the hydraulic performance and the hemolytic performance. For the hydraulic performance, the output flow and the pressure difference between the inlet end and the outlet end of the catheter pump are mainly considered, while for the hemolytic performance, the shear stress of the blood during the pumping process and the smoothness of the blood flow are mainly considered. In some embodiments, by optimizing and improving the structure of the impeller, the hydraulic performance can be improved while the blood damage caused by hemolysis can be reduced.

Figure 2:
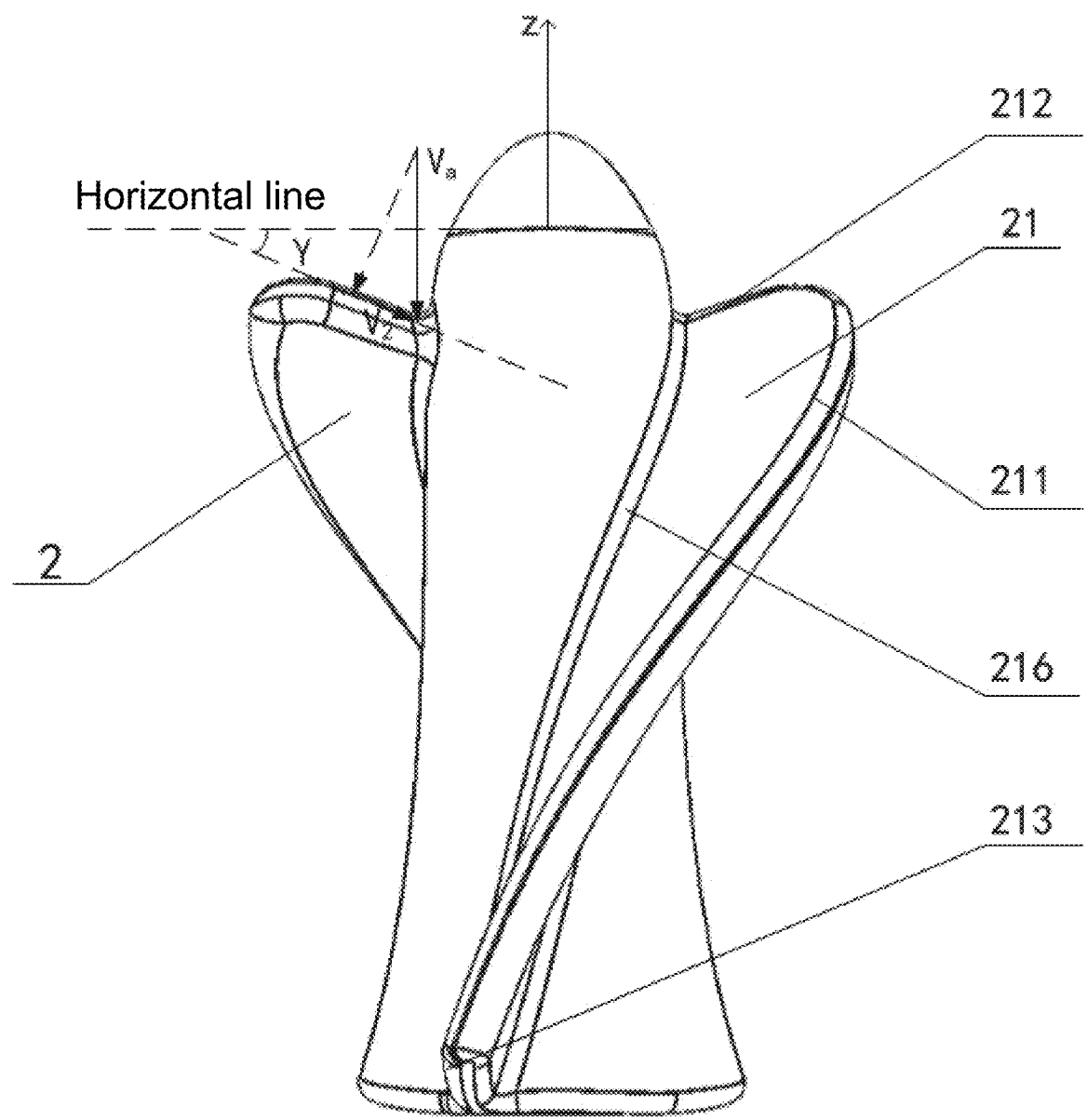
FIG. 2 is a side view of the impeller according to some embodiments of the present disclosure.
Figure 3:
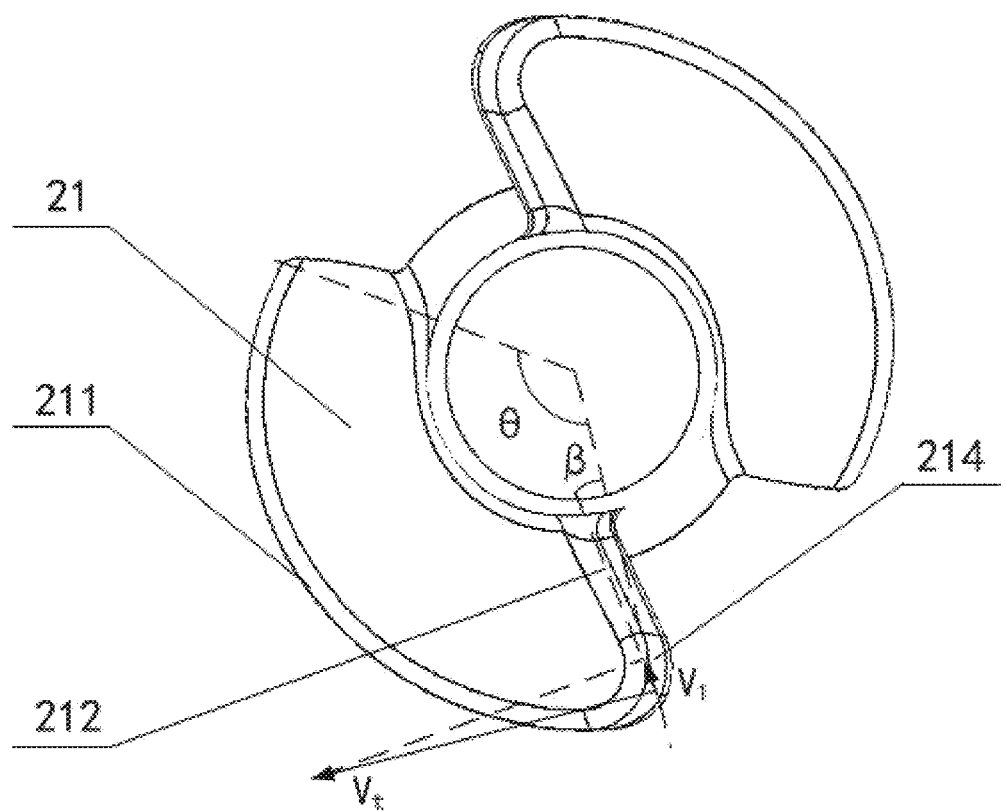
FIG. 3 is a top view of the impeller according to some embodiments of the present disclosure.

FIG. 1 is a front view of the impeller according to some embodiments of the present disclosure. FIG. 2 is a side view of the impeller according to some embodiments of the present disclosure. FIG. 3 is a top view of the impeller according to some embodiments of the present disclosure.

As shown in FIG. 1, FIG. 2, and FIG. 3, in some embodiments, the impeller may comprise a hub 1 and at least one blade 2 fixed to the outer periphery of the hub 1.

The hub 1 may refer to a part of the center of the impeller, the part is connected to a shaft or included in the shaft, and the hub 1 may be used to fix the blade 2 in installation. In some embodiments, the hub may be cylindrical to reduce resistance of blood flow, thereby smoothing blood flow and reducing hemolysis. In some embodiments, the hub 1 may comprise an inlet end 11 and an outlet end 12. The inlet end 11 may refer to an end where blood flows in, and the outlet end 12 may refer to an end where blood flows out. In some embodiments, an outer diameter of the hub 1 may gradually increase from the inlet end 11 to the outlet end 12, and the inlet end 11 of the hub 1 has a smooth top structure. In some embodiments, the inlet end 11 may be a spherical dome or a top structure resembling the spherical dome obtained by rounding an outer edge of a cylinder, which helps to reduce blood pressure when the blood flows through the inlet end 11, and also reduce the generation of turbulence, making the blood flow more stable, and also helping to reduce the flow loss and reduce the occurrence of hemolysis.

The blade 2 may be used for guiding the blood, for example, the blood may flow through a flow channel formed by the blade 2. In some embodiments, the blade 2 is uniform in thickness. In some embodiments, the intersection of an inlet side and an outer edge side of the blade 2 is a smooth transition structure.

In some embodiments, the inlet side of the blade 2 is a side surface corresponding to the thickness of the blade 2 where an inlet edge line 212 is located, the outer edge side is a side surface corresponding to the thickness of the blade 2 where an outer edge profile line 211 is located, and the impeller is rounded at the intersection of the two side surfaces. For the description of the inlet edge line 212 and the outer edge profile line 211, please refer to the related description below.

In some embodiments, the blade 2 may comprise an action surface 21. The action surface 21 may refer to a surface formed by a side surface of the blade 2, the action surface 21 may be a curved surface structure, and the action surface 21 of the blade 2 may pump blood, so the structure of the action surface 21 has a crucial effect on the overall performance of the impeller and even the catheter pump. In some embodiments, the structure of the action surface 21 may be determined by a contour line of the action surface 21.

In some embodiments, the contour line of the action surface 21 is used to form the contour of the action surface 21, and the contour line may comprise the outer edge profile line 211 away from the hub 1 and a hub profile line 216 connected to the outer periphery of the hub 1. The hub profile line 216 and the outer edge profile line 211 form a main streamlined structure of the blade 2. A connection line between a start point of the hub profile line 216 (i.e., an endpoint of the hub profile line 216 close to the inlet end 11) and a start point of the outer edge profile line 211 (i.e., an endpoint of the outer edge profile line 211 close to the inlet end 11) may be the inlet edge line 212. Similarly, a connection line between an endpoint of the hub profile line 216 (i.e., an endpoint of the hub profile line 216 close to the outlet end 12) and an endpoint of the outer edge profile line 211 (i.e., an endpoint of the outer edge profile line 211 close to the outlet end 12) may be an outlet edge line 213.

In some embodiments, the outer edge profile line 211 is a smooth space curve, which means that the action surface 21 smoothly transitions from a side close to the inlet end 11 to a side close to the outlet end 12, during the process of blood flowing from the inlet to the outlet of the impeller, the blood flows smoothly along the curved surface structure of the action surface 21, which helps to reduce the flow loss. Meanwhile, in the process of blood flowing along the action surface 21, the velocity changes gently and the blood distribution is uniform, which helps to reduce the flow dead zone and reduce blood damage.

In some embodiments, an endpoint of the outer edge profile line 211 close to the inlet end 11 is a start point of the profile line 214, and an endpoint of the outer edge profile line 211 close to the outlet end 12 is an end point of the profile line 215.

In some embodiments, a curvature of the outer edge profile line 211 along an axial direction of the hub 1 gradually decreases from the start point of the profile line 214 to the end point of the profile line 215. The greater the curvature of the outer edge profile line 211 along the axial direction of the hub 1 is, the greater the bending degree of the outer edge profile line 211 is, in other words, the greater the degree of deviation of the outer edge profile line 211 from the axial line of the hub 1 is.

In some embodiments, a curvature change rate of the outer edge profile line 211 along the axial direction of the hub 1 gradually decreases from the start point of the profile line 214 to the end point of the profile line 215. In some embodiments, the curvature change rate may gradually decrease according to a certain law, such as a linear decrease. The part of the outer edge profile line 211 close to the start point of the profile line 214 has a large curvature change rate, which can make the blood flow into a flow channel formed by the blade 2 at an impeller inlet along a tangential direction of the outer edge profile line 211, and is helpful to reduce flow disturbance and avoid flow dead zone formation and blood damage. When the outer edge profile line 211 extends to an impeller outlet, the curvature change rate decreases linearly, and the curvature and the curvature change rate of the outer edge profile line 211 along the axial direction of the hub 1 are reduced to the minimum at the end point of the profile line 215, so that the blade maximizes the blood pumping work at the impeller outlet, helping to increase the flow rate and the pressure difference between the impeller inlet and outlet.

In some embodiments, the outer edge profile line 211 of the action surface 21 of the impeller smoothly transitions from the start point of the profile line 214 to the end point of the profile line 215 along the axial direction, and the curvature and the curvature change rate of the outer edge profile line 211 along the axial direction of the hub 1 both gradually decrease, so that the blood flows smoothly when flowing through the action surface 21 of the blade 2, the flow velocity changes smoothly and the blood distribution is even, which helps to improve the hydraulic performance that the impeller can achieve, reduce the flow loss of blood, reduce blood damage and avoid formation of flow dead zone.

In some embodiments, the outer edge profile line 211 is a spiral curve with Gaussian curvature gradient.

The formula of the outer edge profile line 211 is as follows:

$$x = 0.7 + 1.2 * \sin\left(\pi \frac{z + 2.14}{5}\right)$$

$$y = 1.85 - 3.7 e^{-0.5\left(\frac{z-1.3}{1.3}\right)^2}$$

It can be seen from the above formula that the outer edge profile line 211 has continuous derivability along the axial and tangential directions, which makes the action surface 21 smoothly transition from the side close to the inlet end 11 to the side close to the outlet end 12.

The start point of the outer edge profile line 211 corresponds to the point where z=0 in the above formula. As the z value gradually increases (i.e., from the start point of the profile line 214 to the end point of the profile line 215), the curvature and the curvature change rate of the outer edge profile line 211 along the axial direction of the hub 1 gradually decrease.

As shown in FIG. 1, in some embodiments, the inclined angle between the tangent line of the start point of the profile line 214 and the tangential velocity $V_t$ of the start point of the profile line 214 is the inlet inclined angle α of the outer edge profile line 211.

In some embodiments, the angle of the inlet inclined angle α may be 25°-35°.

In some embodiments, the angle of the inlet inclined angle α may comprise, but is not limited to, 25°, 26°, 27°, 28°, 29°, 30°, 31°, 32°, 33°, 34°, or 35°.

As shown in FIG. 1, in some embodiments, the resultant velocity of the axial velocity $V_a$ (in the axial direction of the hub 1) at the start point of the profile line 214 and the tangential velocity $V_t$ (in a circumferential direction of the hub 1) at the start point of the profile line 214 is the relative velocity V at the start point of the profile line 214. The inclined angle between the relative velocity V at the start point of the profile line 214 and the tangential velocity $V_t$ (or circumference, horizontal line) at the start point of the profile line 214 is the inlet installation angle $a_m$ of the outer edge profile line 211. The axial velocity $V_a$ and the tangential velocity $V_t$ may be obtained based on the velocity of blood flowing into the start point of the profile line 214.

In some embodiments, the angle of the inlet installation angle $a_m$ comprises, but is not limited to, 0°, 1°, 2°, 3°, 4° or 5°.

In some embodiments, the inlet inclined angle α is greater than the inlet installation angle $a_m$. When the inlet inclined angle α is greater than the inlet installation angle $a_m$, there is an angle difference between the inlet inclined angle α and the inlet installation angle $a_m$, and the angle difference is an inclined angle α formed by the relative velocity V and the tangent line of the start point of the profile line 214. The inclined angle a is also called an inflow angle of attack.

When blood flows at a low speed, the inflow angle of attack may inhibit the flow separation of blood when blood flows through the action surface 21, reduce the inflow flow loss when blood enters the impeller, increase the hydraulic performance, and help to reduce blood damage.

In some embodiments, the angle difference between the inlet inclined angle α and the inlet installation angle $a_m$ is less than or equal to 5°.

Figure 4:
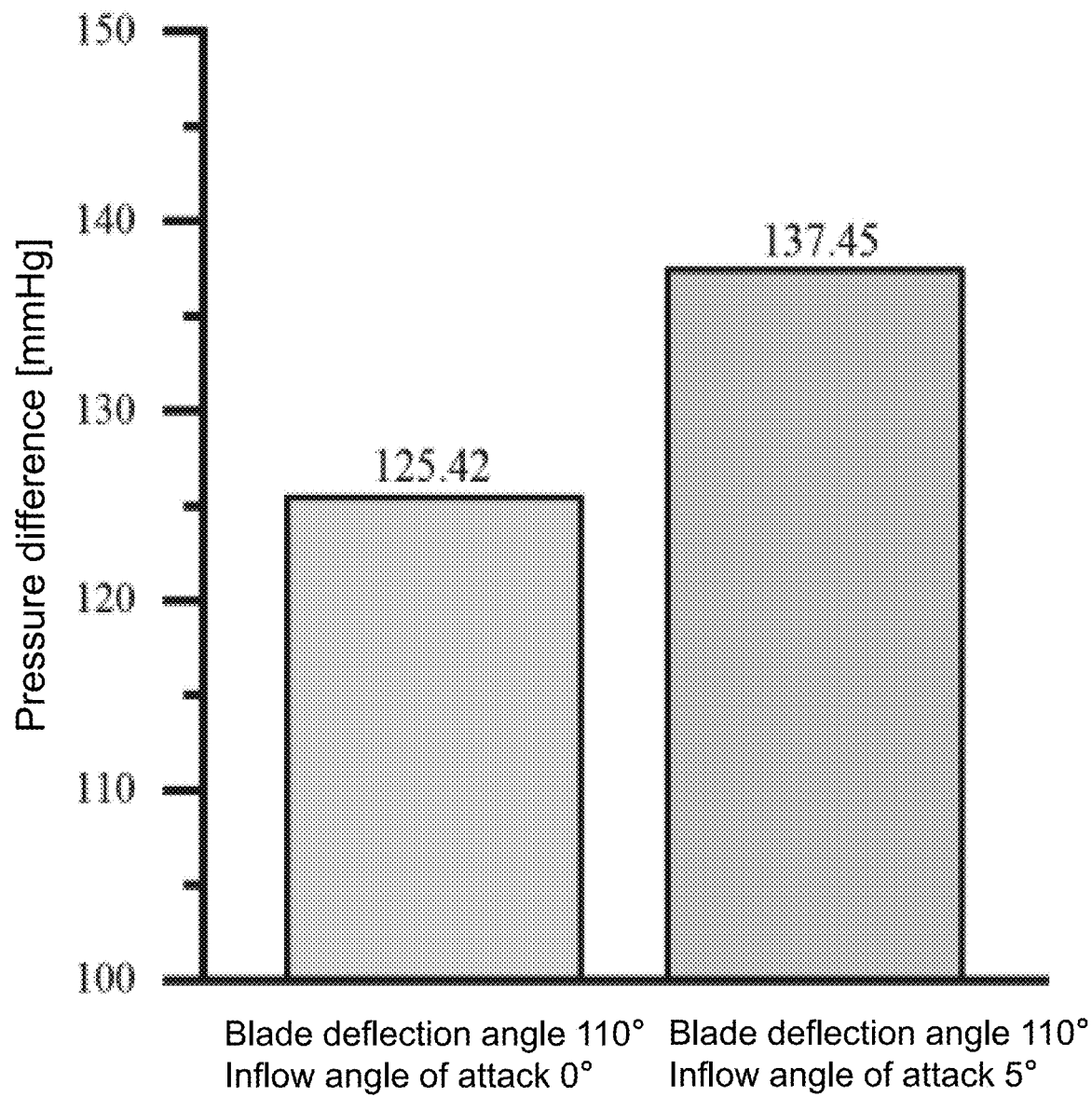
FIG. 4 is a comparison histogram of pressure differences of two structures where an inflow angle of attack of the impeller is 0° and 5° respectively according to some embodiments of the present disclosure.
Figure 5:
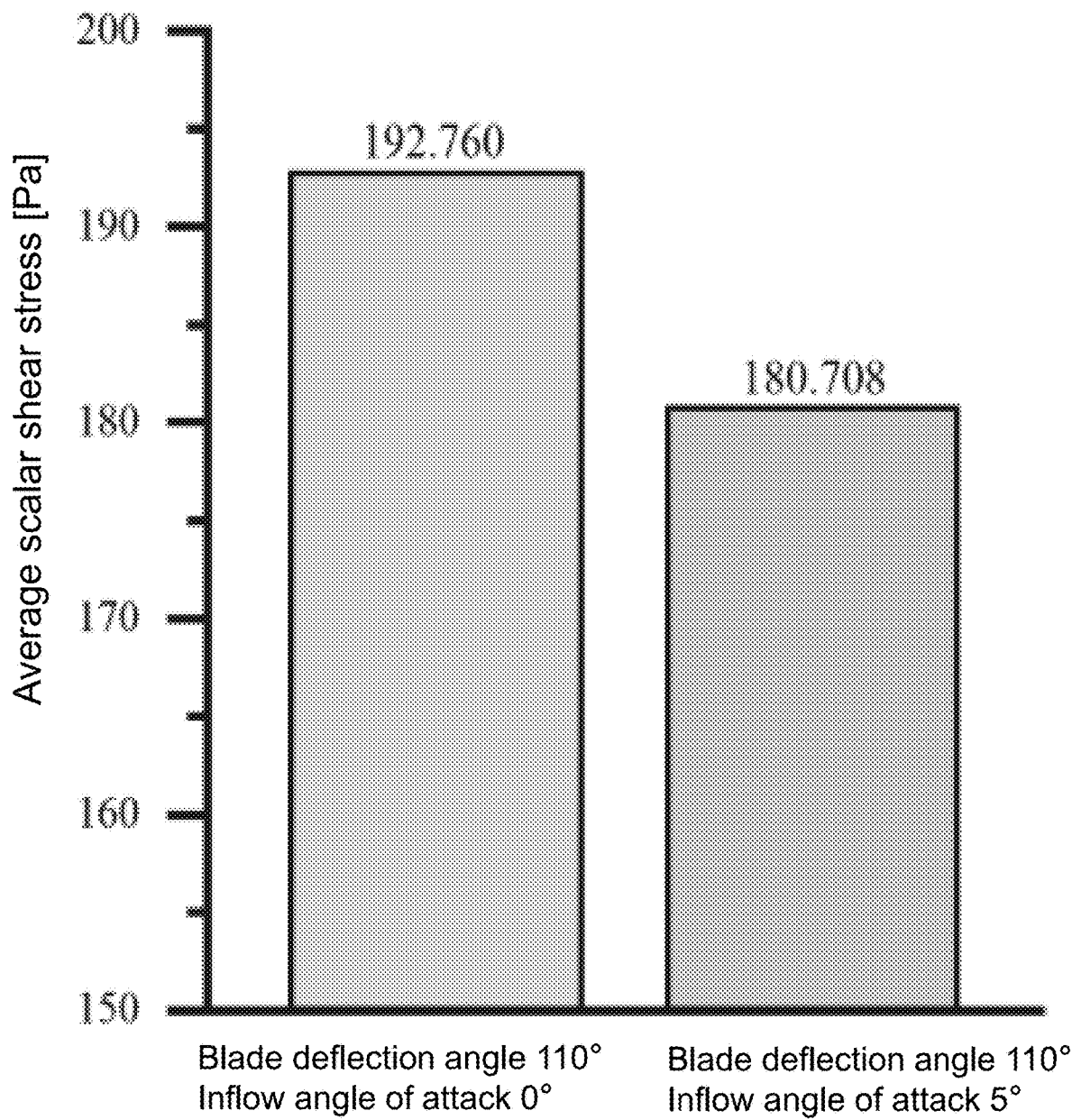
FIG. 5 is a comparison histogram of an average scalar shear stress of two structures where the inflow angle of attack of the impeller is 0° and 5° respectively according to some embodiments of the present disclosure.
Figure 6:
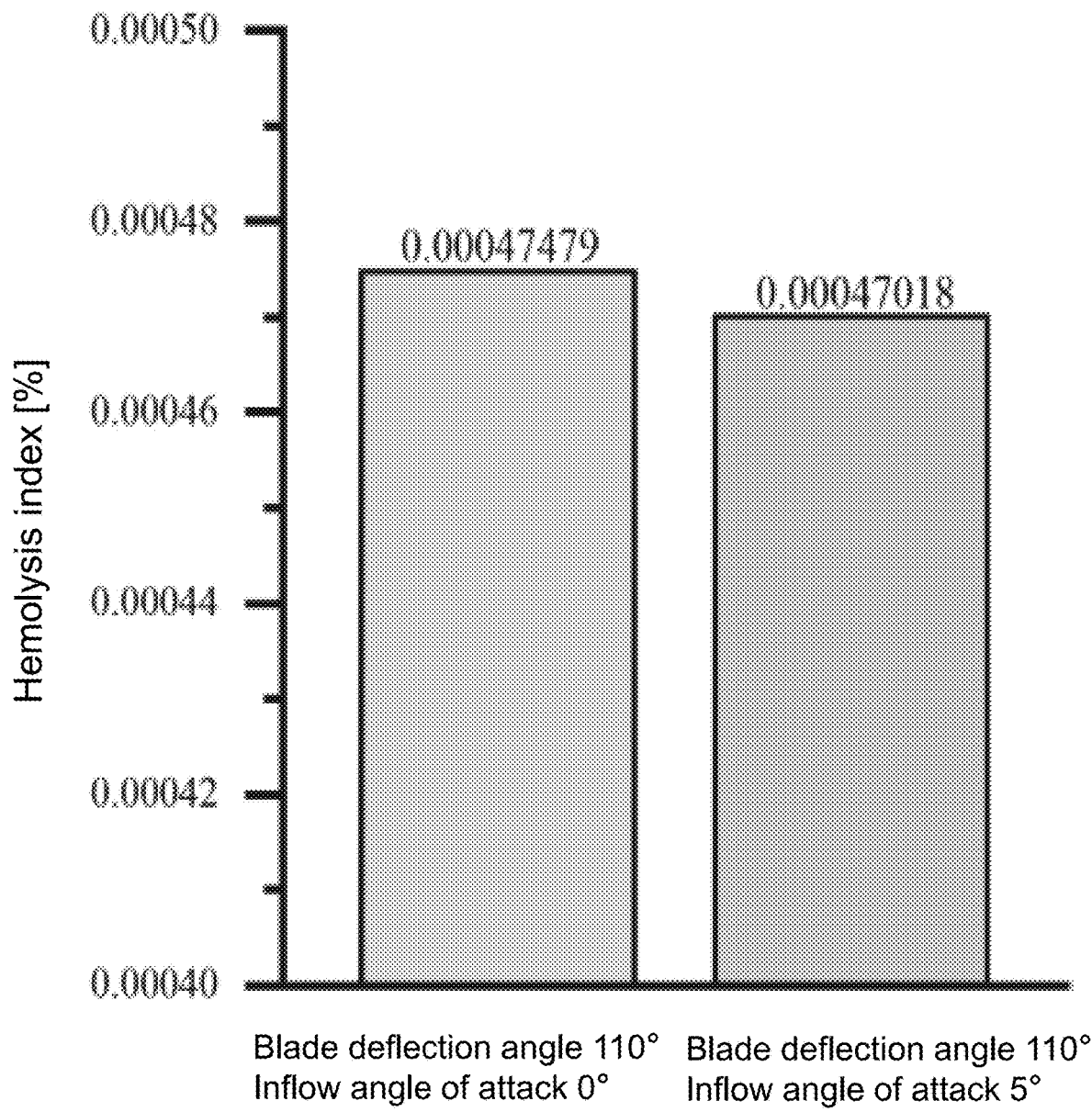
FIG. 6 is a comparison histogram of hemolysis indices of two structures where the inflow angle of attack of the impeller is 0° and 5° respectively according to some embodiments of the present disclosure.
Figure 7:
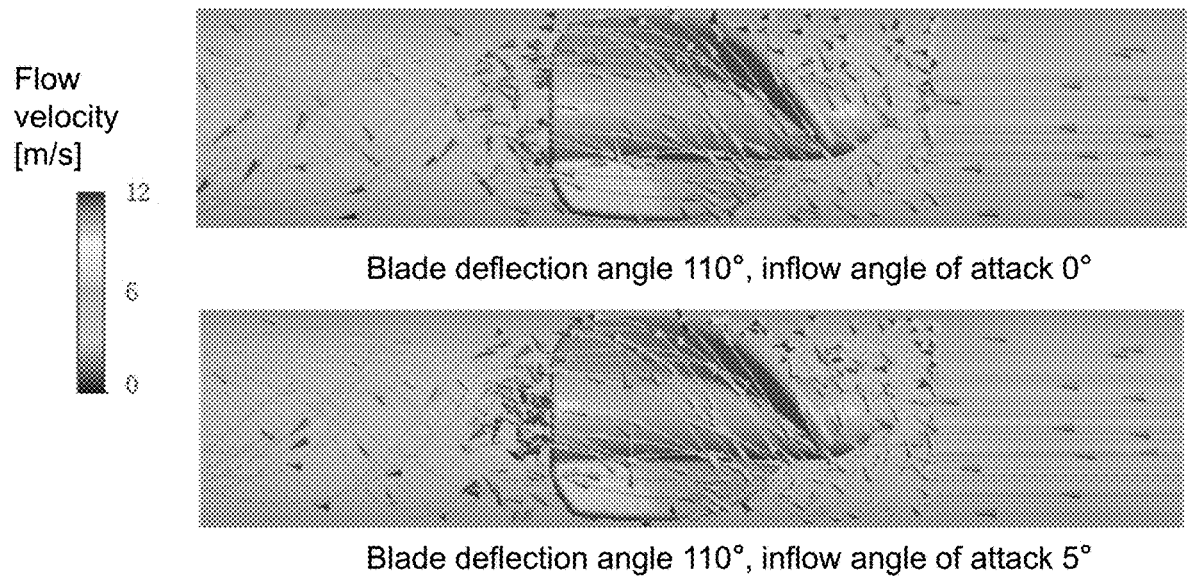
FIG. 7 is comparison diagram of three-dimensional flow fields of two structures where the inflow angle of attack of the impeller is 0° and 5° respectively according to some embodiments of the present disclosure.
Figure 8:
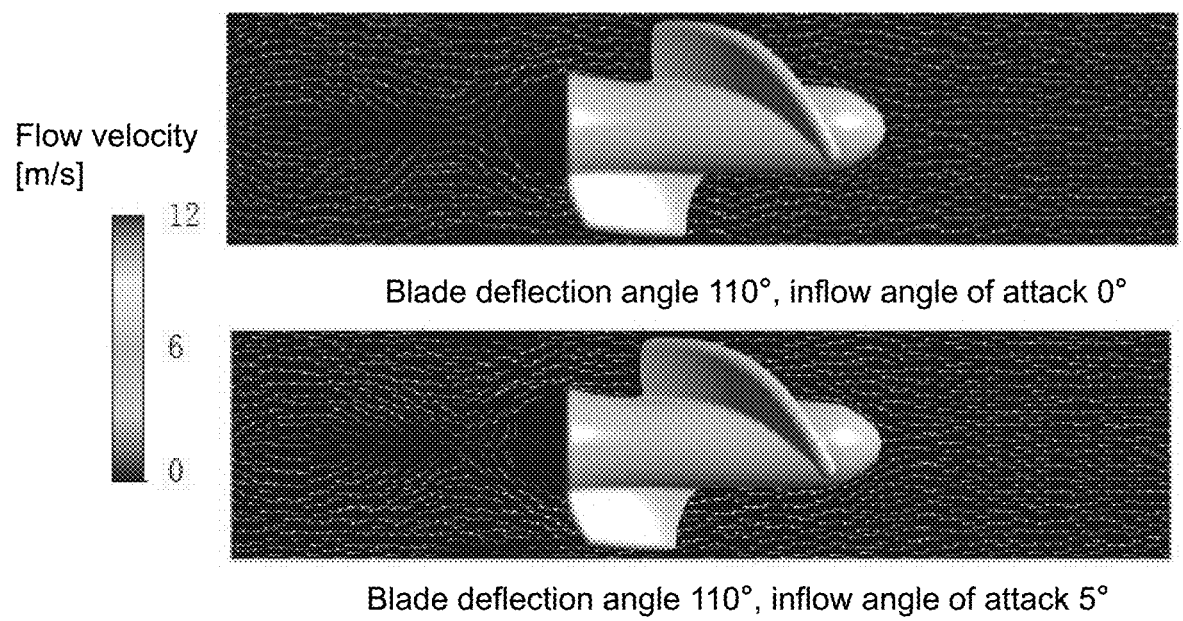
FIG. 8 is a comparison diagram of radial cross-sectional flow fields of two structures where the inflow angle of attack of the impeller is 0° and 5° respectively according to some embodiments of the present disclosure.
Figure 9:
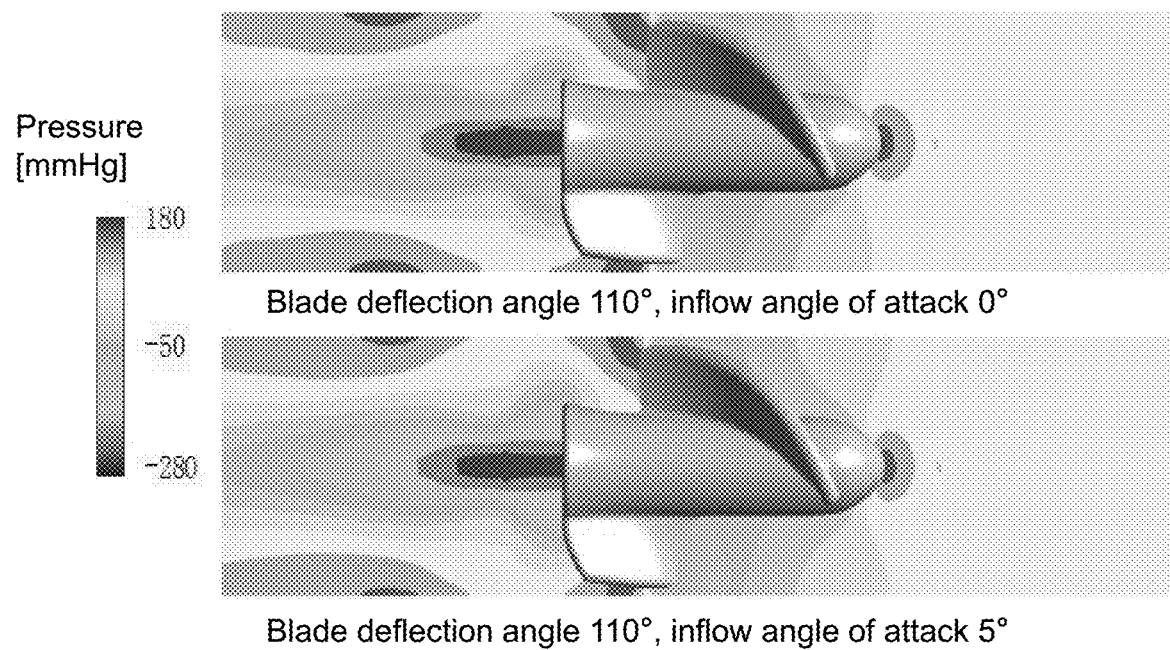
FIG. 9 is a comparison diagram of radial cross-sectional pressure of two structures where the inflow angle of attack of the impeller is 0° and 5° respectively according to some embodiments of the present disclosure.
Figure 10:
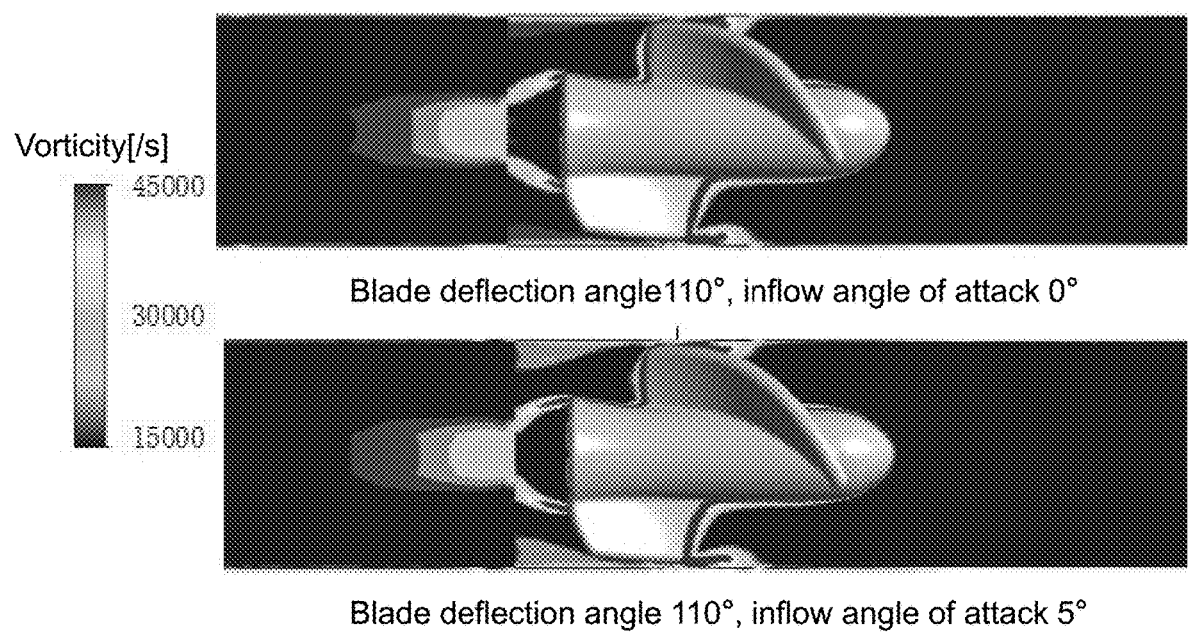
FIG. 10 is a comparison diagram of radial cross-sectional vorticity of two structures where the inflow angle of attack of the impeller is 0° and 5° respectively according to some embodiments of the present disclosure.
Figure 11:
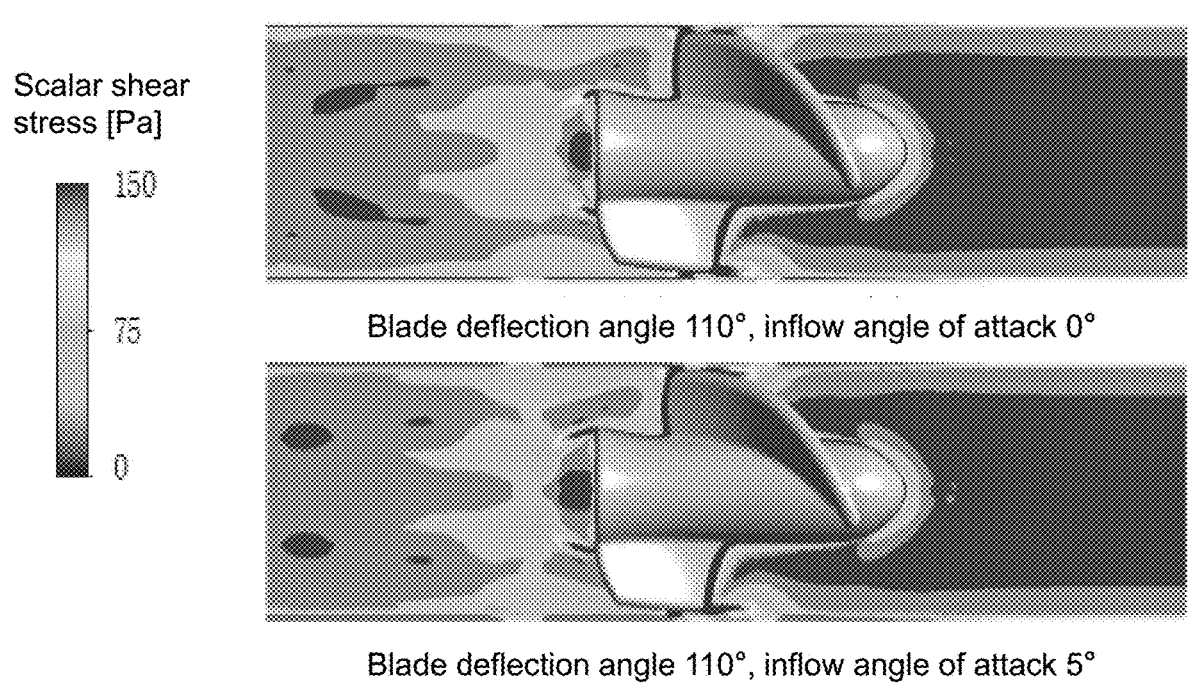
FIG. 11 is a comparison diagram of radial cross-sectional scalar shear stress of two structures where the inflow angle of attack of the impeller is 0° and 5° respectively according to some embodiments of the present disclosure.
Figure 12:
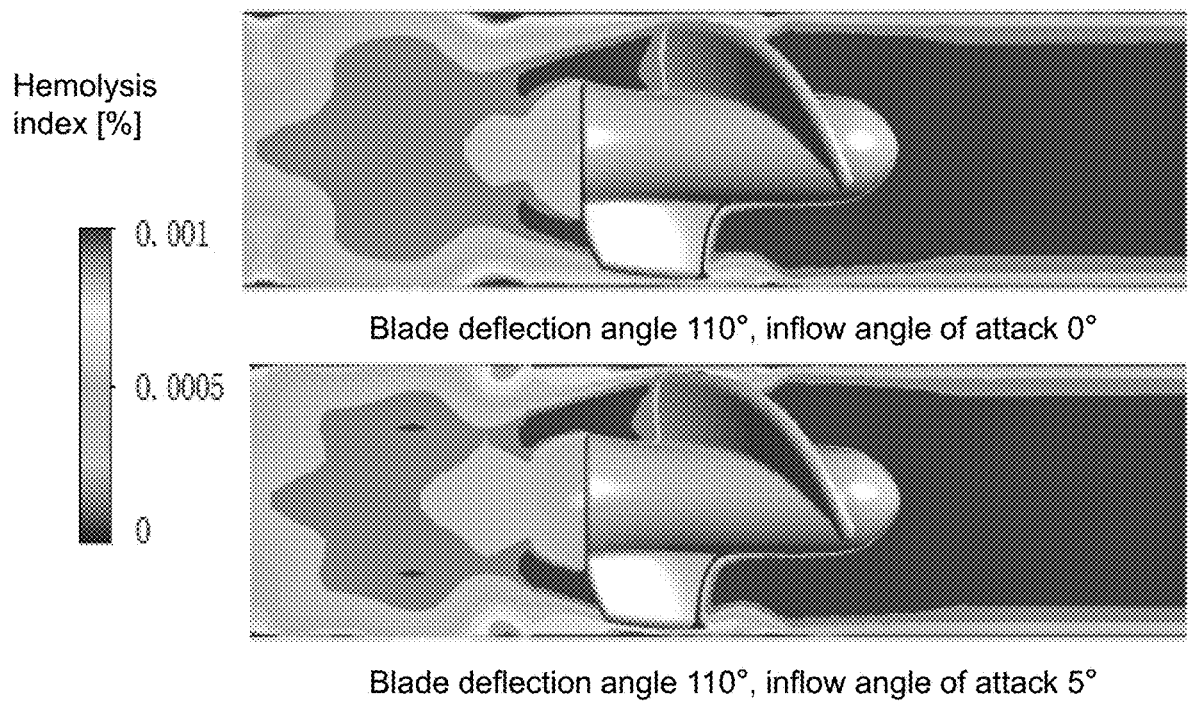
FIG. 12 is a comparison diagram of radial cross-sectional hemolysis indices of two structures where the inflow angle of attack of the impeller is 0° and 5° respectively according to some embodiments of the present disclosure.
Figure 13:
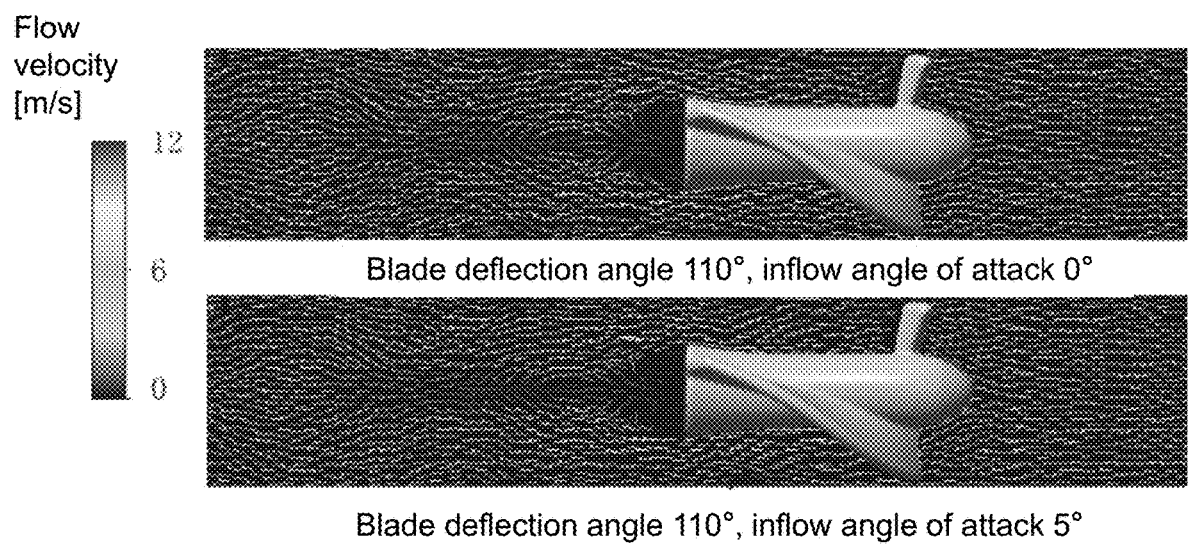
FIG. 13 is another comparison diagram of radial cross-sectional flow fields of two structures where the inflow angle of attack of the impeller is 0° and 5° respectively according to some embodiments of the present disclosure.
Figure 14:
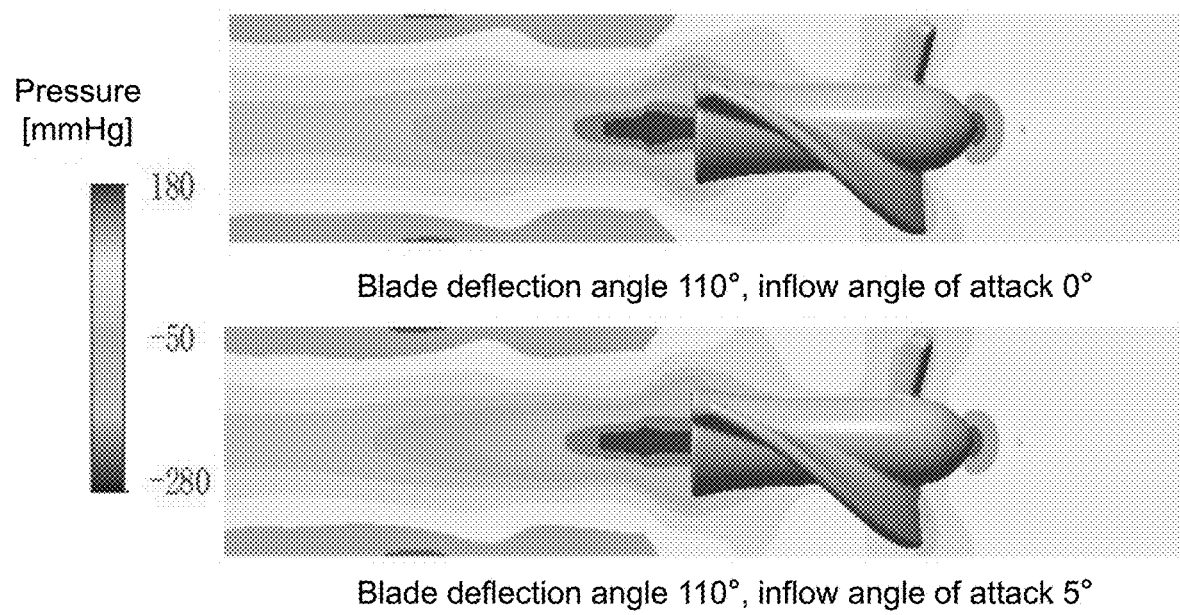
FIG. 14 is another comparison diagram of radial cross-sectional pressure of two structures where the inflow angle of attack of the impeller is 0° and 5° respectively according to some embodiments of the present disclosure.
Figure 15:
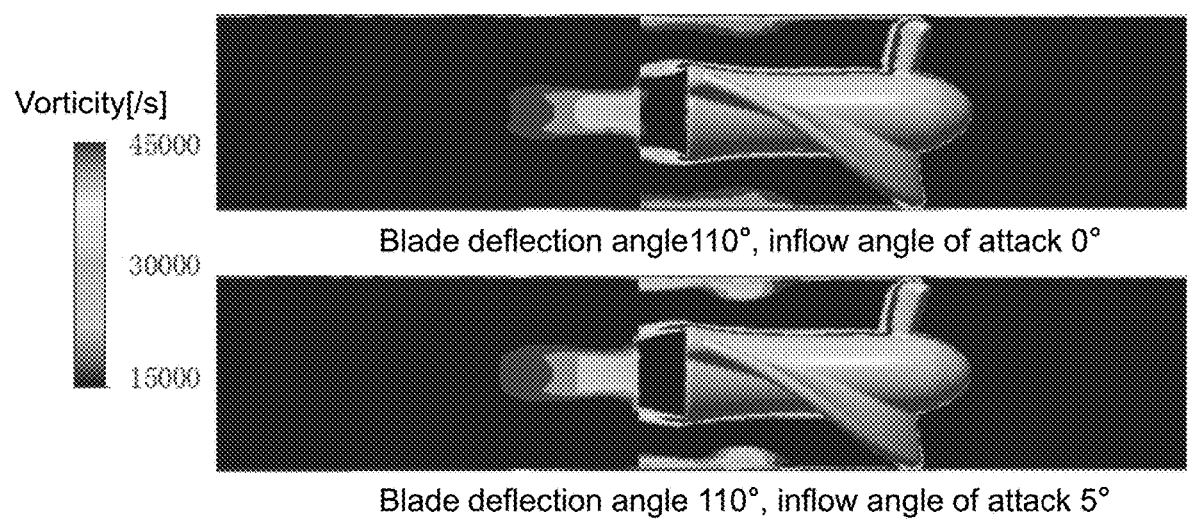
FIG. 15 is another comparison diagram of radial cross-sectional vorticity of two structures where the inflow angle of attack of the impeller is 0° and 5° respectively according to some embodiments of the present disclosure.
Figure 16:
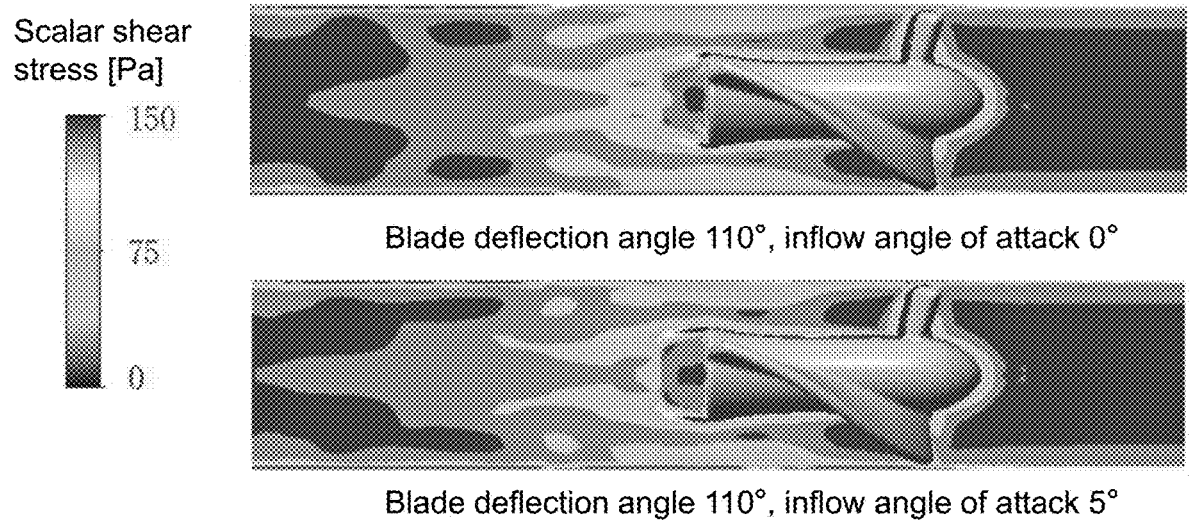
FIG. 16 is another comparison diagram of radial cross-sectional scalar shear stress of two structures where the inflow angle of attack of the impeller is 0° and 5° respectively according to some embodiments of the present disclosure.
Figure 17:
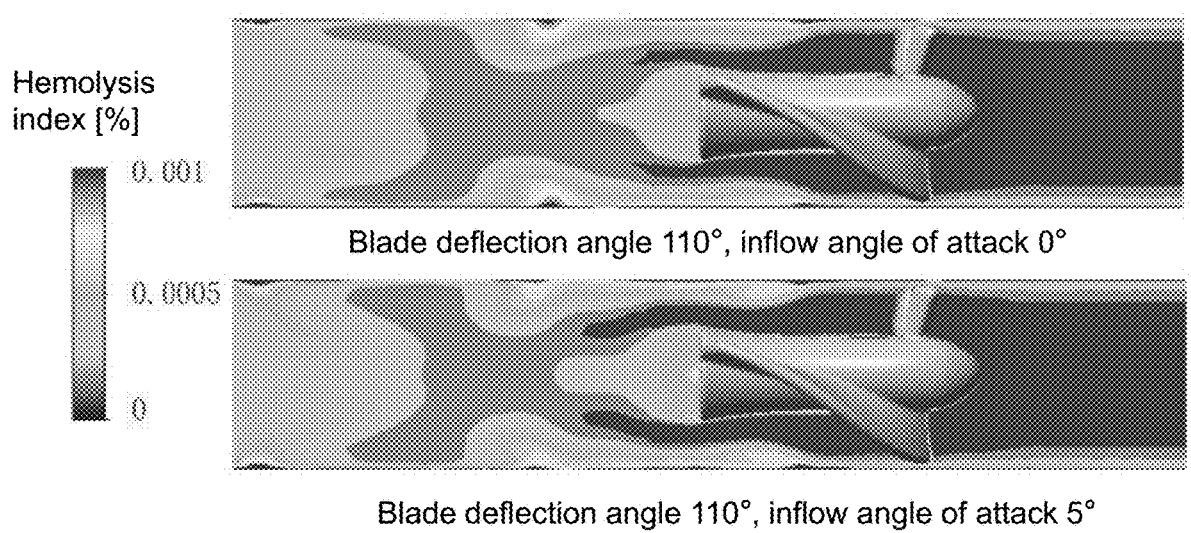
FIG. 17 is another comparison diagram of radial cross-sectional hemolysis indices of two structures where the inflow angle of attack of the impeller is 0° and 5° respectively according to some embodiments of the present disclosure.

FIG. 4 is a comparison histogram of pressure differences of two structures where the inflow angle of attack of the impeller is 0° and 5° respectively according to some embodiments of the present disclosure. FIG. 5 is a comparison histogram of average scalar shear stress of two structures where the inflow angle of attack of the impeller is 0° and 5° respectively according to some embodiments of the present disclosure. FIG. 6 is a comparison histogram of hemolysis indices of two structures where the inflow angle of attack of the impeller is 0° and 5° respectively according to some embodiments of the present disclosure. FIG. 7 is a comparison diagram of three-dimensional flow fields of two structures where the inflow angle of attack of the impeller is 0° and 5° respectively according to some embodiments of the present disclosure. FIG. 8 is a comparison diagram of radial cross-sectional flow fields of two structures where the inflow angle of attack of the impeller is 0° and 5° respectively according to some embodiments of the present disclosure. FIG. 9 is a comparison diagram of radial cross-sectional pressure of two structures where the inflow angle of attack of the impeller is 0° and 5° respectively according to some embodiments of the present disclosure. FIG. 10 is a comparison diagram of radial cross-sectional vorticity of two structures where the inflow angle of attack of the impeller is 0° and 5° respectively according to some embodiments of the present disclosure. FIG. 11 is a comparison diagram of radial cross-sectional scalar shear stress of two structures where the inflow angle of attack of the impeller is 0° and 5° respectively according to some embodiments of the present disclosure. FIG. 12 is a comparison diagram of radial cross-sectional hemolysis indices of two structures where the inflow angle of attack of the impeller is 0° and 5° respectively according to some embodiments of the present disclosure. FIG. 13 is another comparison diagram of radial cross-sectional flow fields of two structures where the inflow angle of attack of the impeller is 0° and 5° respectively according to some embodiments of the present disclosure. FIG. 14 is another comparison diagram of radial cross-sectional pressure of two structures where the inflow angle of attack of the impeller is 0° and 5° respectively according to some embodiments of the present disclosure. FIG. 15 is another comparison diagram of radial cross-sectional vorticity of two structures where the inflow angle of attack of the impeller is 0° and 5° respectively according to some embodiments of the present disclosure. FIG. 16 is another comparison diagram of radial cross-sectional scalar shear stress of two structures where the inflow angle of attack of the impeller is 0° and 5° respectively according to some embodiments of the present disclosure. FIG. 17 is another comparison diagram of radial cross-sectional hemolysis indices of two structures where the inflow angle of attack of the impeller is 0° and 5° respectively according to some embodiments of the present disclosure.

Two impeller structures with the inflow angle of attack of 0° and 5° are selected for simulation experiments to compare the hydraulic performance and the hemolytic performance achieved by the two impeller structures. The results are shown in FIG. 4-FIG. 17.

It can be seen from FIG. 4 that in the structure with the inflow angle of attack of 5°, the pressure difference between the impeller inlet and the impeller outlet is significantly higher than that of the impeller structure with the inflow angle of attack of 0°. Correspondingly, the impeller under this structure may achieve a larger head. Compared with the structure with the inflow angle of attack of 0°, the impeller of the structure with the inflow angle of attack of 5° has better hydraulic performance.

It can be seen from FIG. 5 that in the structure with the inflow angle of attack of 5°, the average scalar shear stress generated by the impeller during rotation is significantly lower than that of the impeller structure with the inflow angle of attack of 0°. The effect of lower average scalar shear stress is also reflected in FIG. 6. It can be seen that the hemolysis index in the structure with the inflow angle of attack of 5° is significantly lower than that of the structure with the inflow angle of attack of 0°, indicating that the impeller structure with the inflow angle of attack of 5° may ensure that the pumped blood has better physiological indicators and better hemolysis performance.

On the basis of the above data, the difference between the hydraulic performance and the hemolytic performance of the two impeller structures when the inflow angle of attack is 0° and 5° may be more intuitively displayed through FIG. 7-FIG. 17.

FIG. 7 is a comparison diagram of the three-dimensional flow fields of two impeller structures. Arrows with different color depths in the drawing represent velocity values of fluid when the fluid flows through the impeller. It can be seen from FIG. 7 that the blood is in the same state before entering the impeller inlet, and obvious flow separation occurs in the structure with the inflow angle of attack being 0° when exiting the impeller, and does not occur to the structure with the inflow angle of attack of 5°. Compared with the structure with the inflow angle of attack of 0°, the impeller with the inflow angle of attack of 5° has better hydraulic performance.

FIG. 8 shows the comparison diagram of the radial cross-sectional flow fields of the two impeller structures, and the velocity values of the blood when flowing through the impeller are also represented by arrows with different color depths. It can also be seen that in the structure with the inflow angle of attack of 0°, when the blood flows out of the impeller, the flow separation occurs, and blood turbulence also occurs. In the structure with the inflow angle of attack of 5°, the blood flow is more stable and uniform, and has better hydraulic performance.

FIG. 9 shows the comparison diagram of the radial cross-sectional pressure of the two impeller structures. Different colors are used in the drawing to represent the pressure distribution of the fluid when the fluid flows through the impeller. It can be seen that in the structure with the inflow angle of attack of 5°, the pressure at the impeller outlet is lower, and there is a more obvious pressure difference between the impeller inlet and the impeller outlet. Compared with the structure with the inflow angle of attack of 0°, the impeller with the inflow angle of attack of 5° has better hydraulic performance.

FIG. 10 shows the comparison diagram of the radial cross-sectional vorticity of the two impeller structures, and different colors are used in the drawing to represent the distribution of the vorticity of the blood flowing through the impeller. It can be seen that in the structure with the inflow angle of attack of 5°, the vorticity is more uniformly distributed around the impeller, avoiding vortex concentration, making the blood flow more smoothly through the impeller, and helping to reduce flow loss. Compared with the structure with the inflow angle of attack of 0°, the impeller with the inflow angle of attack of 5° has better hydraulic performance.

FIG. 11 shows the comparison diagram of the radial cross-sectional scalar shear stress of the two impeller structures, and the distribution of the scalar shear stress of different color fluids flowing through the impeller is shown in the drawing. It can be seen that under the structure with the inflow angle of attack of 5°, the scalar shear stress is relatively small, especially at the impeller outlet.

FIG. 12 shows the comparison diagram of the radial cross-sectional hemolysis indices of the two impeller structures, and different colors are used in the figure to represent the distribution of the hemolysis indices of the fluid flowing through the impeller. Corresponding to the scalar shear stress, the hemolysis index is lower under the structure with the inflow angle of attack of 5°, especially after the blood flows out of the impeller. Compared with the structure with the inflow angle of attack of 0°, the impeller with the inflow angle of attack of 5° has better hemolysis performance.

FIG. 13-FIG. 17 show another radial section of the impeller to carry out the simulation experiments carried out in the above FIG. 8-FIG. 12, so as to further corroborate the hydraulic performance and the hemolytic performance achieved by the impeller under the two impeller structures of the above-mentioned inflow angle of attack of 0° and the inflow angle of attack of 5°. The experimental effects shown in FIG. 13-FIG. 17 are the same as those shown in FIG. 8-FIG. 12, and will not be repeated here.

It can be seen from the above simulation experiments that, compared with the structure with the inflow angle of attack of 0°, the impeller with the inflow angle of attack of 5° can achieve higher hydraulic performance and reduce the hemolysis of the pumped blood.

In some embodiments, the calculation formula of the inlet installation angle $a_m$ is as follows:

$$a_m = \arctan\frac{V_a}{V_t}$$

the calculation formula of the axial velocity $V_a$ at the start point of the profile line 214 is as follows:

$$V_a = \frac{Q}{A} = \frac{4Q}{\pi D^2}.$$

In the formula, Q is a preset flow rate, A is a cross-sectional area of a pipe of the catheter pump at the installation of the impeller, and D is an inner diameter of the catheter pump at the installation of the impeller.

The calculation formula of the tangential velocity $V_t$ at the start point of the profile line 214 is as follows:

$$V_t = \omega\frac{D}{2}.$$

In the formula, ω is the preset rotational velocity of the blade 2.

The calculation formula of the inlet inclined angle α of the outer edge profile line 211 is as follows:

$$\alpha = a + a_m$$

Taking the preset flow Q as 5 L/min, the inner diameter D of the catheter pump as 5 mm, and the preset rotational velocity as 35000 RPM (revolution/min) as an example to calculate the inlet inclined angle α:

$$V_a = \frac{Q}{A} = \frac{4Q}{\pi D^2} = 4.244 \text{ m/s}$$

$$V_t = \omega\frac{D}{2} = 9.163 \text{ m/s}$$

$$a_m = \arctan\frac{V_a}{V_t} = 0.4338 \text{ rad}$$

The result 0.4338 rad is expressed in radians, which is converted into an angle value approximately equal to 25°, that is, the installation angle is 25°.

According to the simulation experiment of the inflow angle of attack, the angle value of the inflow angle of attack is 5°, then $$\alpha = a + a_m \approx 30°$$

In some embodiments, the angle value of the inlet inclined angle α may also be calculated by the aforementioned curve formula of the outer edge profile line 211, and the specific process is as follows:

First, taking the derivative of the curve formula:

$$\frac{\partial y}{\partial z}\bigg|z=0 = -3.7 * e^{-0.5} * \left(-1 * \frac{\left(\frac{0-1.3}{1.3}\right)}{1.3}\right) = -1.73$$

Then performing the arctangent operation on the obtained result:

$$\arctan\left(\frac{\partial y}{\partial z}\bigg|z=0\right) \approx -60°$$

The obtained angle is the inclined angle between the tangent line of the start point of the profile line 214 of and a z-axis direction. As shown in FIG. 1, the angle of the inlet inclined angle α may be calculated is 30°.

As shown in FIG. 3, in some embodiments, the inclined angle between the axial plane where the start point of the profile line 214 is located and the axial plane where the end point of the profile line 215 is located is the blade deflection angle θ, and the blade deflection angle θ is 900-150°.

In some embodiments, the blade deflection angle θ comprises, but is not limited to, 90°, 95°, 100°, 105°, 110°, 115°, 120°, 125°, 130°, 135°, 140°, 145° and 150°.

The axial plane where the start point of the profile line 214 is located represents a plane where the start point of the profile line 214 and a central axis of the hub 1 are located. Because this plane is jointly defined by a straight line (i.e., the central axis of the hub 1) and a point outside the straight line (the start point of the profile line 214), so the plane is uniquely determined. Similarly, the axial plane where the end point of the profile line 215 is located represents a plane where the start point of the profile line 214 and the central axis of the hub 1 are located, and the plane is also uniquely determined.

The blade deflection angle θ in FIG. 3 may be more intuitively understood as that, in a top projection view of the impeller, an inclined angle, formed by a connection line between the start point of the profile line 214 and the axis of the hub 1 as well as a connection line between the end point of the profile line 215 and the axis of the hub 1, is the blade deflection angle θ. The size of the blade deflection angle θ reflects the length of the circumferential extension of each blade 2 on the hub 1.

Figure 18:
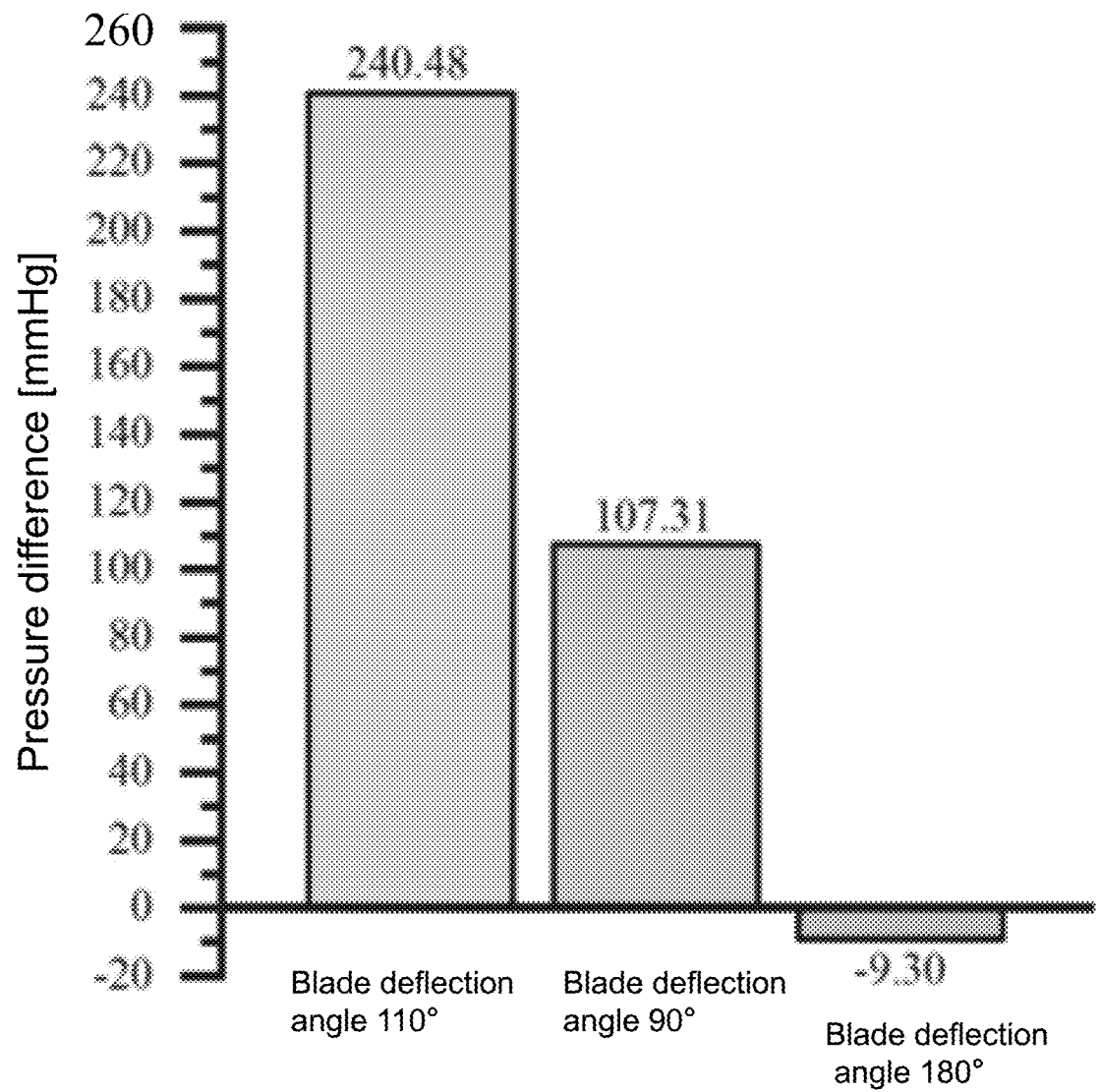
FIG. 18 is a comparison histogram of pressure differences of three structures where the blade deflection angle of the impeller is 90°, 110° and 180° respectively according to some embodiments of the present disclosure.
Figure 19:
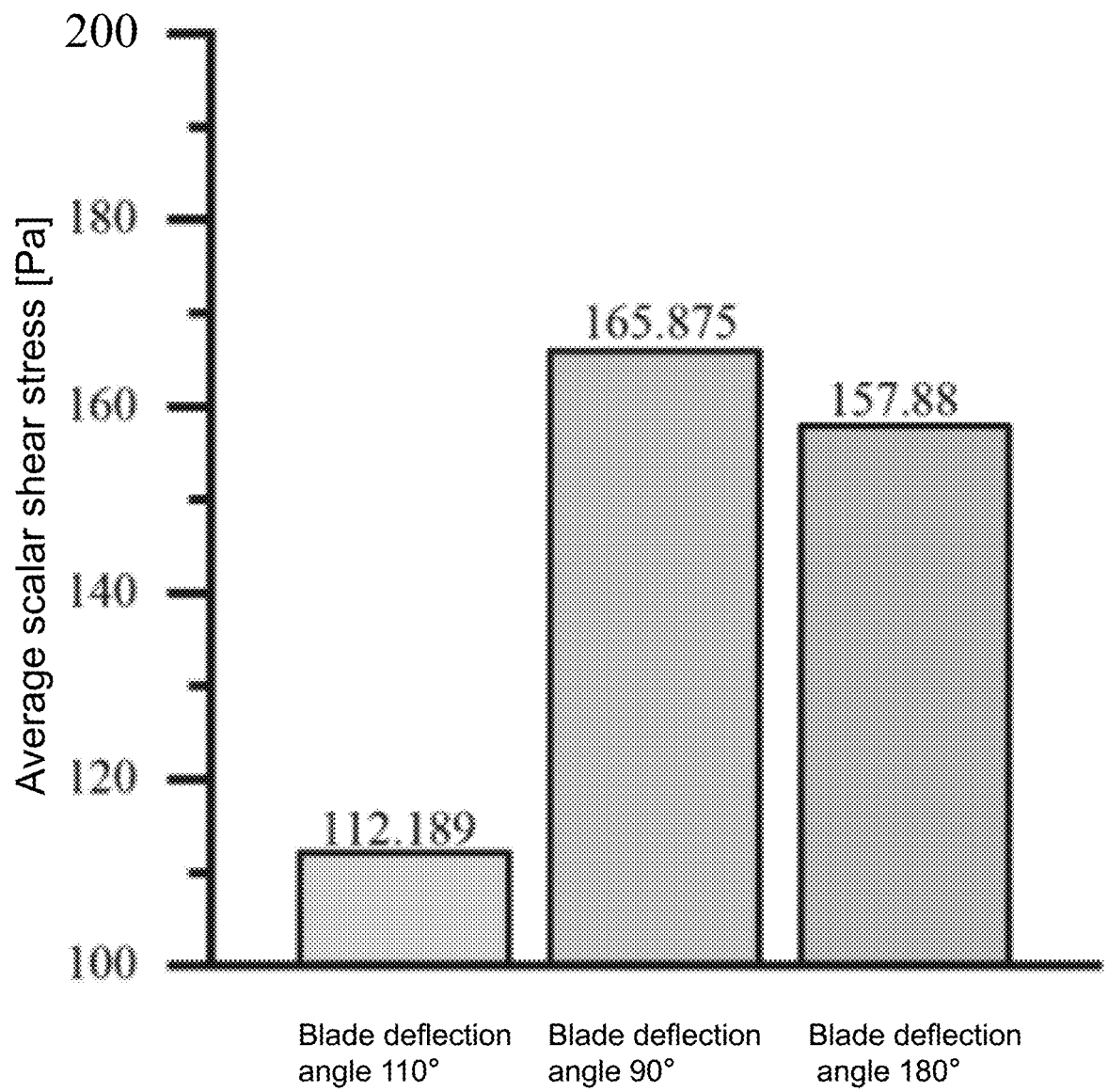
FIG. 19 is a comparison histogram of average scalar shear stress of three structures where the blade deflection angle of the impeller is 90°, 110° and 180° respectively according to some embodiments of the present disclosure.
Figure 20:
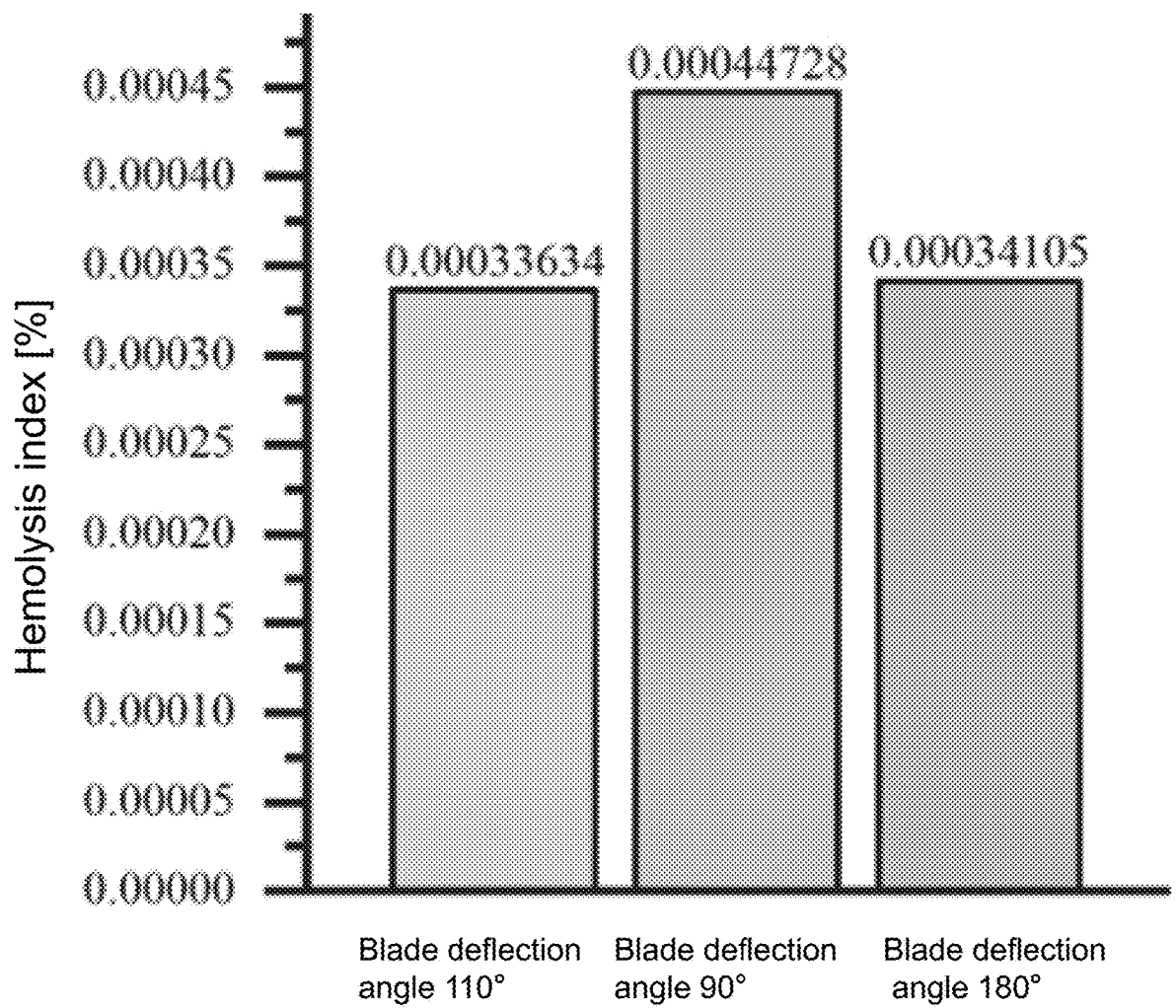
FIG. 20 is a comparison histogram of hemolysis indices of three structures where the blade deflection angle of the impeller is 90°, 110° and 180° respectively according to some embodiments of the present disclosure.
Figure 21:
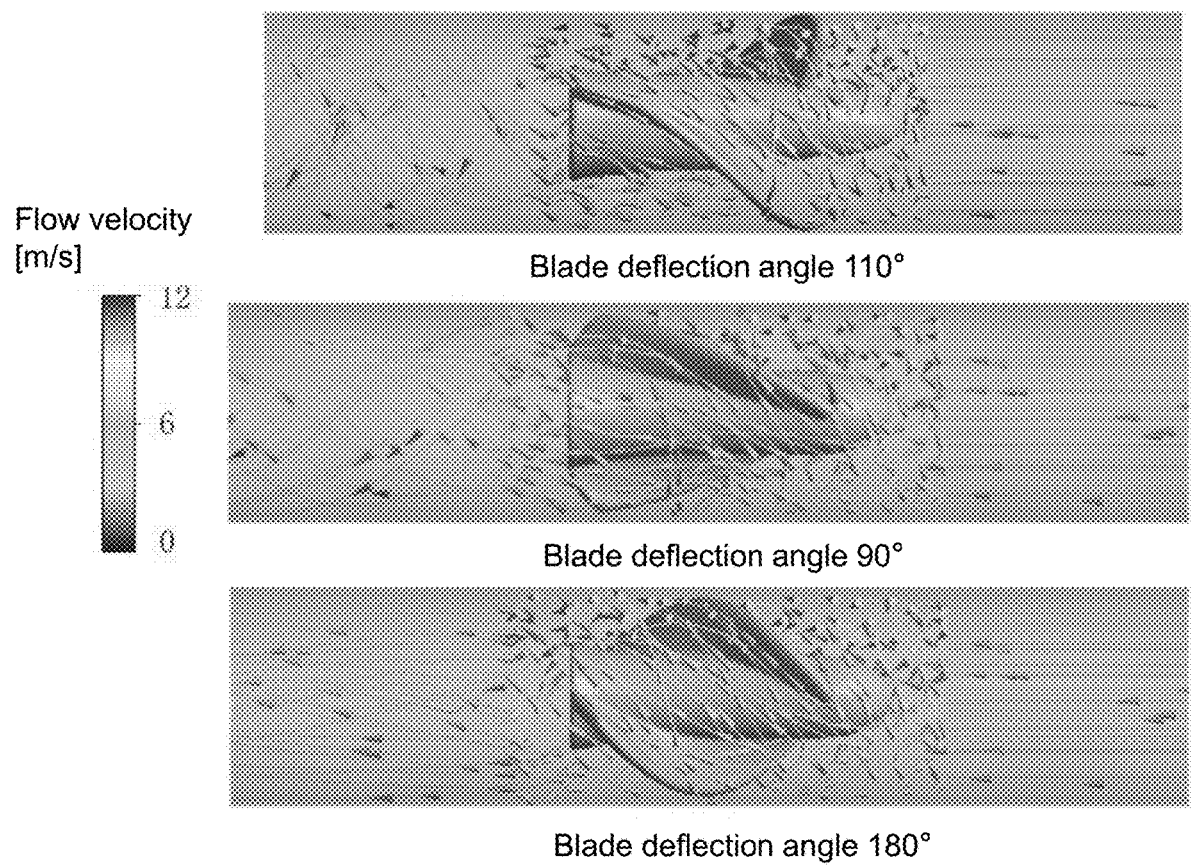
FIG. 21 is a comparison diagram of three-dimensional flow fields of three structures where the blade deflection angle of the impeller is 90°, 110° and 180° respectively according to some embodiments of the present disclosure.
Figure 22:
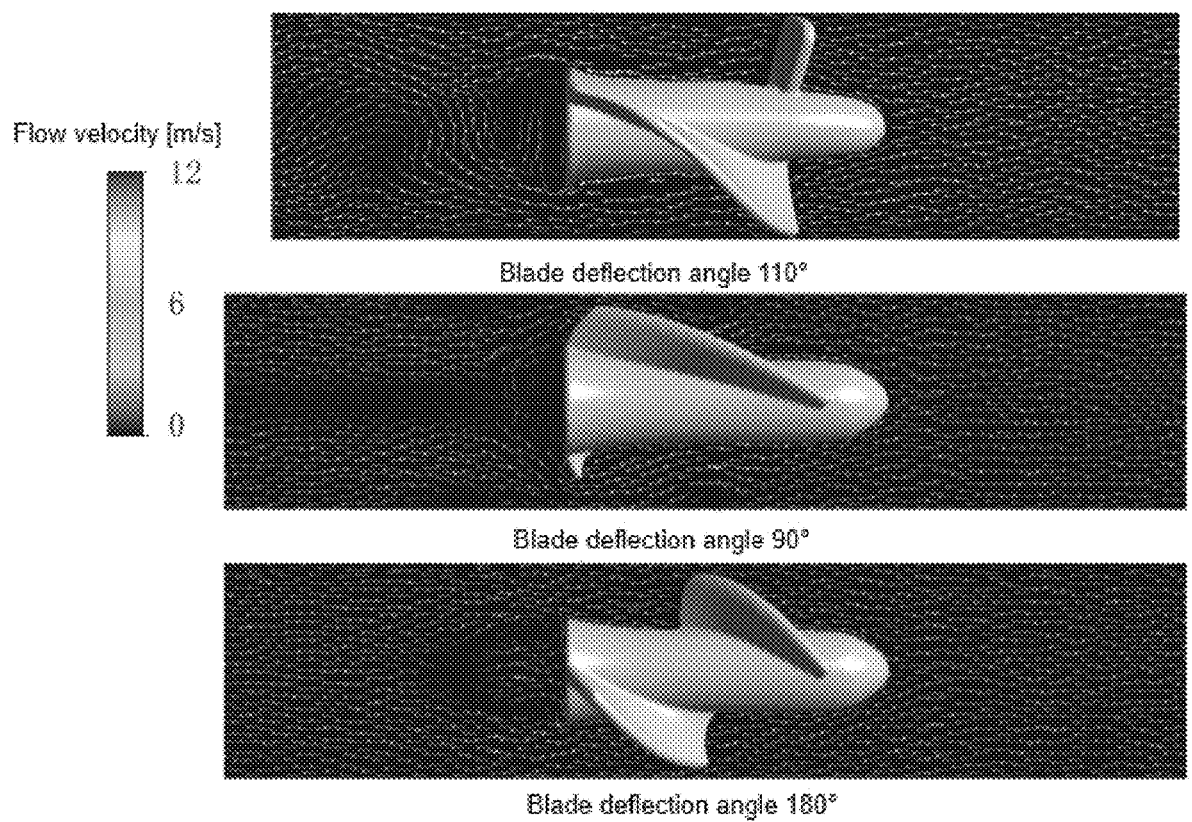
FIG. 22 is a comparison diagram of radial cross-sectional flow fields of three structures where the blade deflection angle of the impeller is 90°, 110° and 180° respectively according to some embodiments of the present disclosure.
Figure 23:
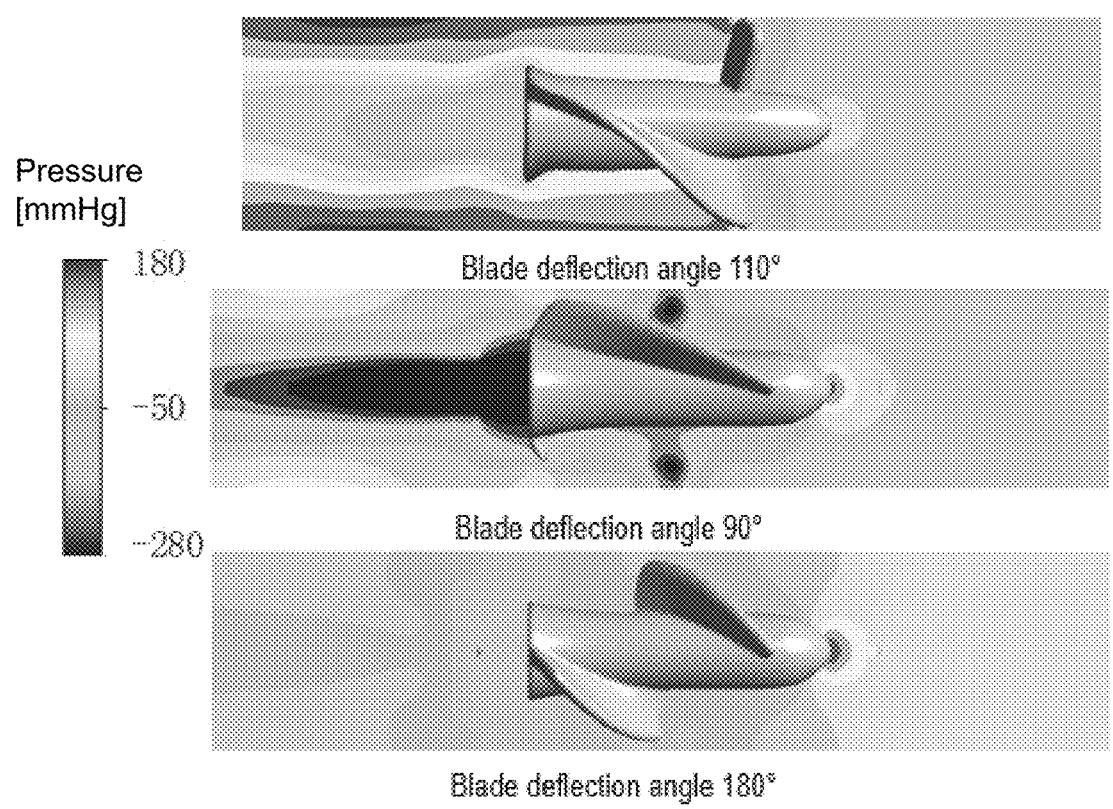
FIG. 23 is a comparison diagram of radial cross-sectional pressure of three structures where the blade deflection angle of the impeller is 90°, 110° and 180° respectively according to some embodiments of the present disclosure.
Figure 24:
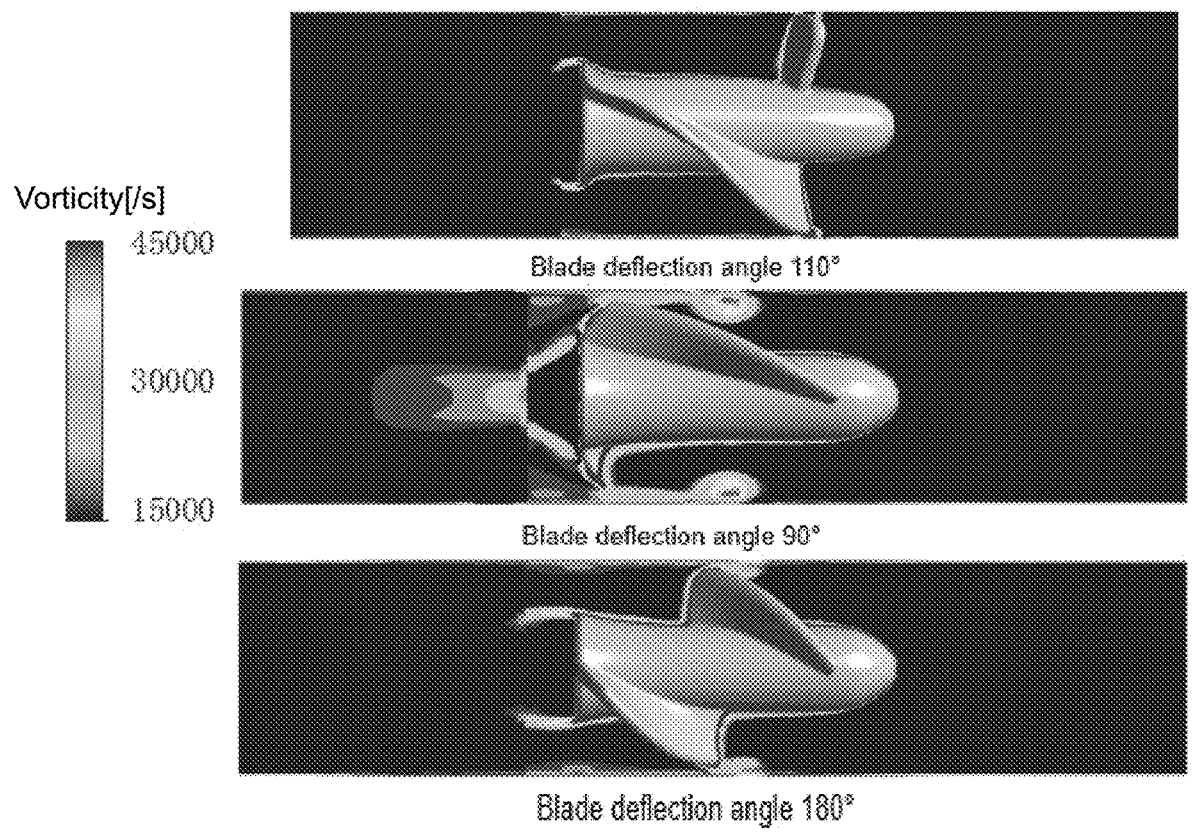
FIG. 24 is a comparison diagram of radial cross-sectional vorticity of three structures where the blade deflection angle of the impeller is 90°, 110° and 180° respectively according to some embodiments of the present disclosure.
Figure 25:
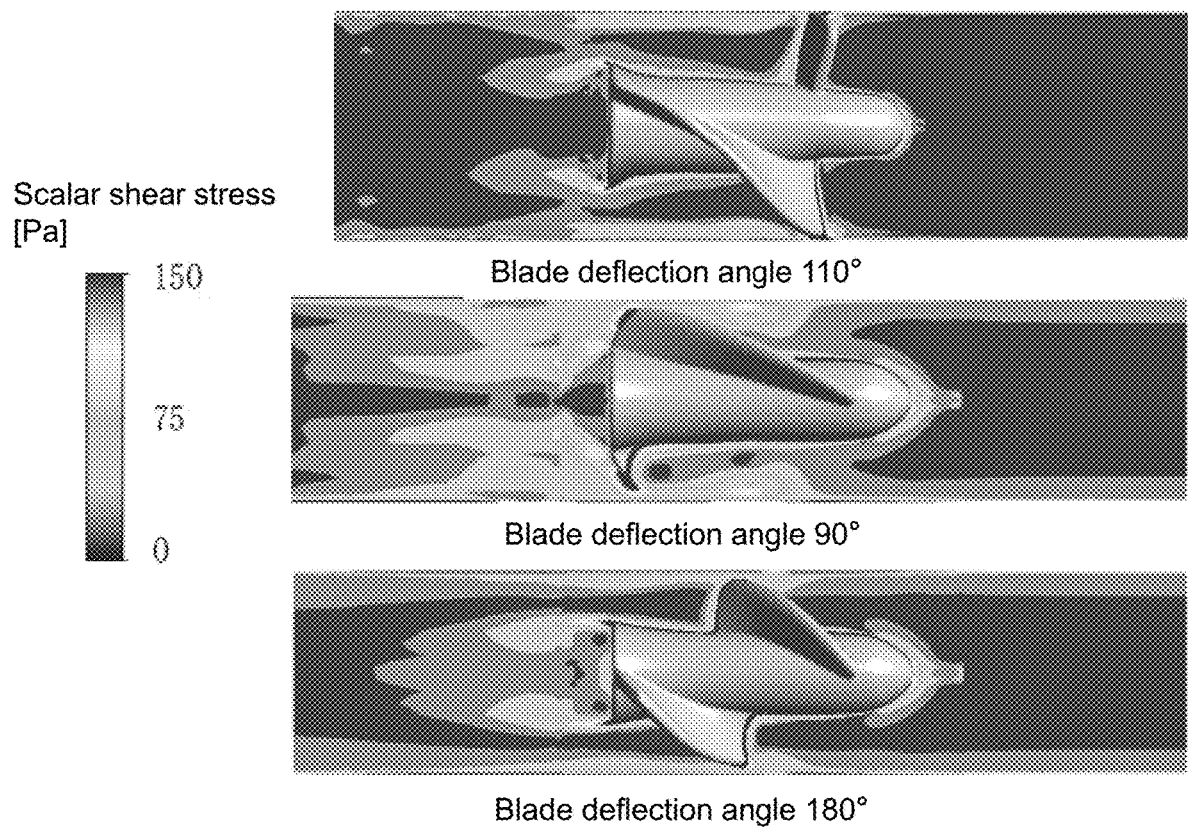
FIG. 25 is a comparison diagram of radial cross-sectional scalar shear stress of three structures where the blade deflection angle of the impeller is 90°, 110° and 180° respectively according to some embodiments of the present disclosure.
Figure 26:
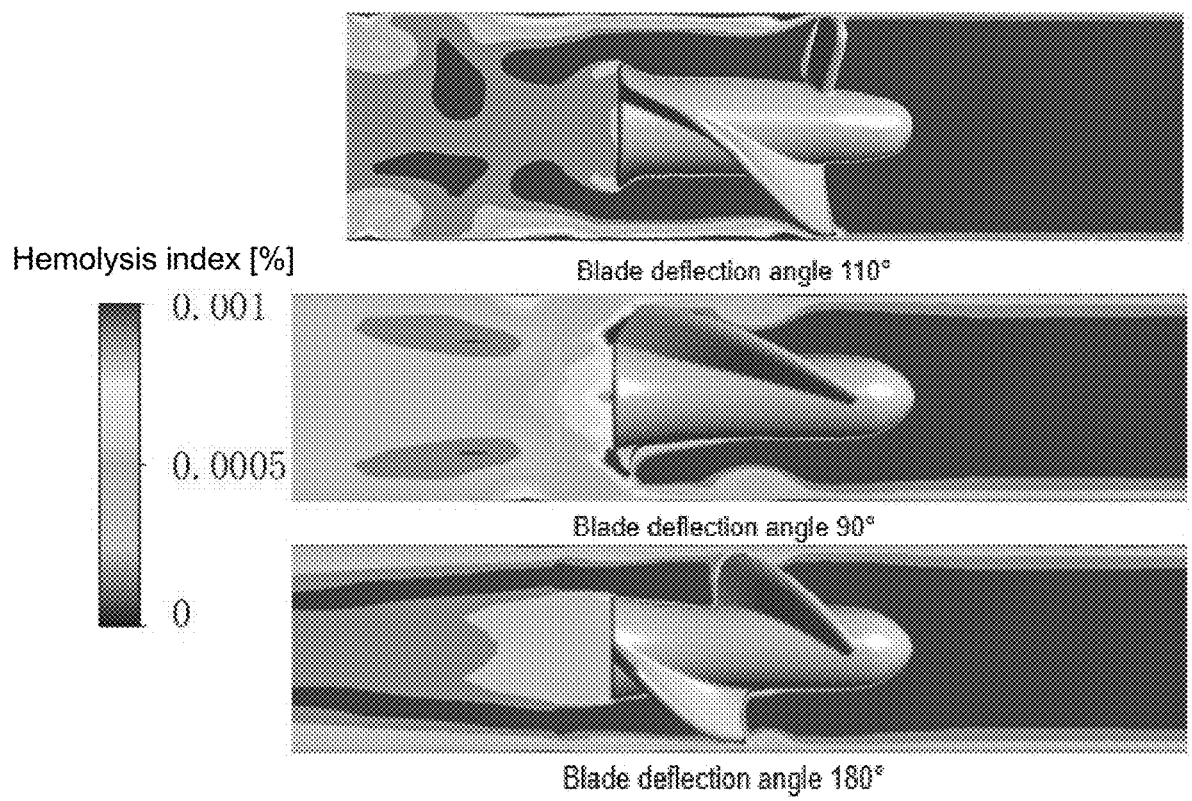
FIG. 26 is a comparison diagram of radial cross-sectional hemolysis indices of three structures where the blade deflection angle of the impeller is 90°, 110° and 180° respectively according to some embodiments of the present disclosure.
Figure 27:
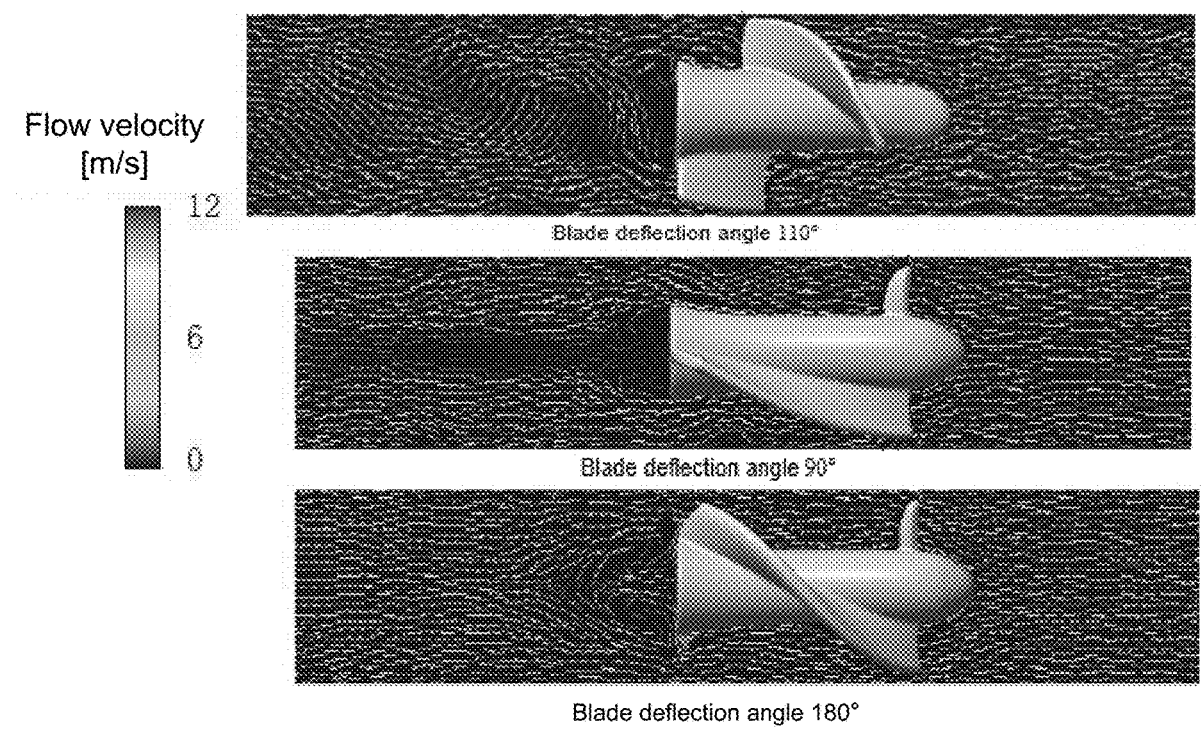
FIG. 27 is another comparison diagram of radial cross-sectional flow fields of three structures where the blade deflection angle of the impeller is 90°, 110° and 180° respectively according to some embodiments of the present disclosure.
Figure 28:
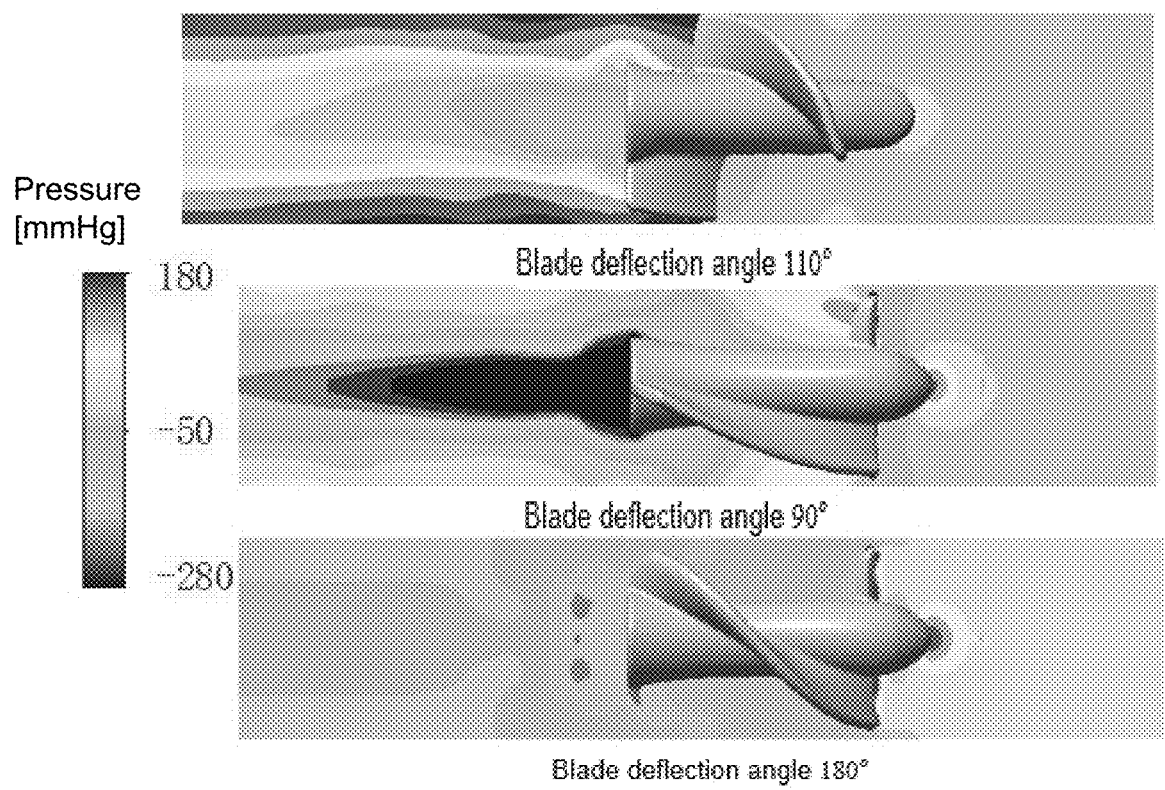
FIG. 28 is another comparison diagram of radial cross-sectional pressure of three structures where the blade deflection angle of the impeller is 90°, 110° and 180° respectively according to some embodiments of the present disclosure.
Figure 29:
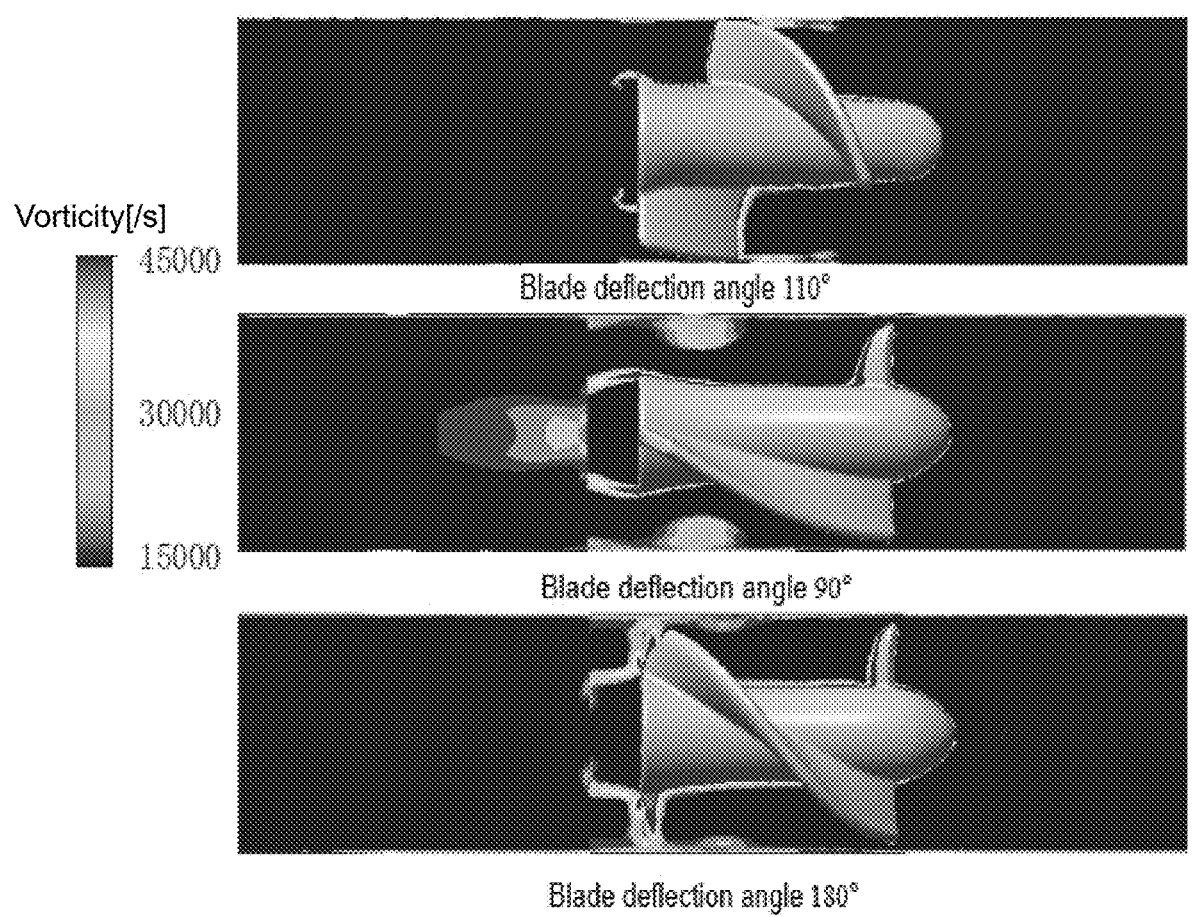
FIG. 29 is another comparison diagram of radial cross-sectional vorticity of three structures where the blade deflection angle of the impeller is 90°, 110° and 180° respectively according to some embodiments of the present disclosure.
Figure 30:
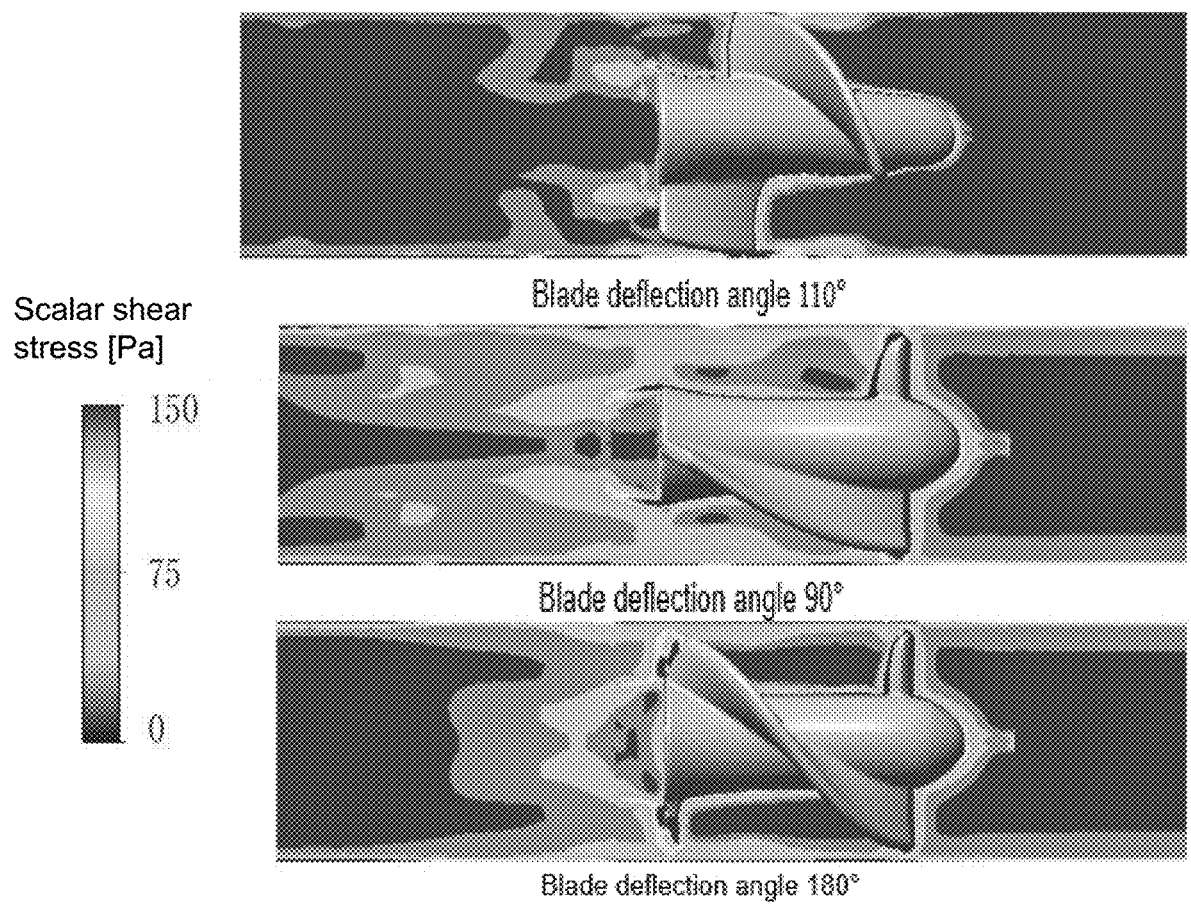
FIG. 30 is another comparison diagram of radial cross-sectional scalar shear stress of three structures where the blade deflection angle of the impeller is 90°, 110° and 180° respectively according to some embodiments of the present disclosure.
Figure 31:
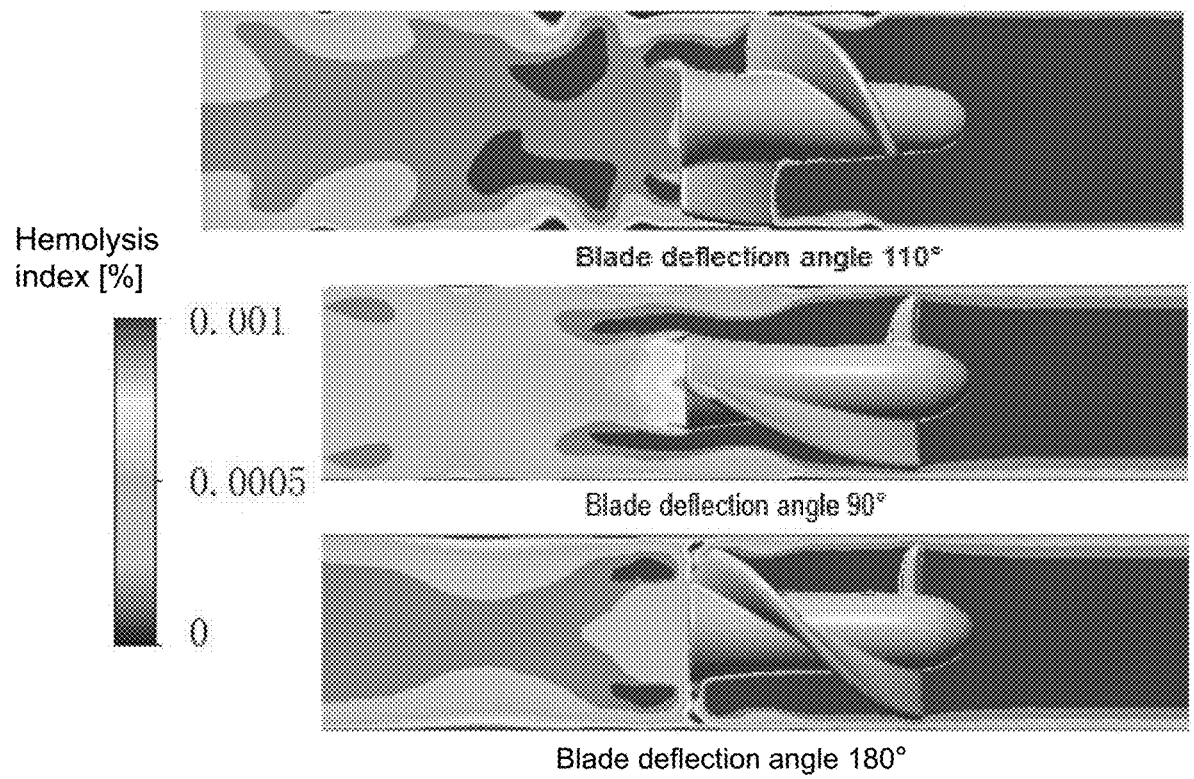
FIG. 31 is another comparison diagram of radial cross-sectional hemolysis indices of three structures where the blade deflection angle of the impeller is 90°, 110° and 180° respectively according to some embodiments of the present disclosure.

FIG. 18 is a comparison histogram of pressure differences of three structures where the blade deflection angle of the impeller is 90°, 110° and 180° respectively according to some embodiments of the present disclosure. FIG. 19 is a comparison histogram of average scalar shear stress of three structures where the blade deflection angle of the impeller is 90°, 110° and 180° respectively according to some embodiments of the present disclosure. FIG. 20 is a comparison histogram of hemolysis indices of three structures where the blade deflection angle of the impeller is 90°, 110° and 180° respectively according to some embodiments of the present disclosure. FIG. 21 is a comparison diagram of three-dimensional flow fields of three structures where the blade deflection angle of the impeller is 90°, 110° and 180° respectively according to some embodiments of the present disclosure. FIG. 22 is a comparison diagram of radial cross-sectional flow fields of three structures where the blade deflection angle of the impeller is 90°, 110° and 180° respectively according to some embodiments of the present disclosure. FIG. 23 is a comparison diagram of radial cross-sectional pressure of three structures where the blade deflection angle of the impeller is 90°, 110° and 180° respectively according to some embodiments of the present disclosure. FIG. 24 is a comparison diagram of radial cross-sectional vorticity of three structures where the blade deflection angle of the impeller is 90°, 110° and 180° respectively according to some embodiments of the present disclosure. FIG. 25 is a comparison diagram of radial cross-sectional scalar shear stress of three structures where the blade deflection angle of the impeller is 90°, 110° and 180° respectively according to some embodiments of the present disclosure. FIG. 26 is a comparison diagram of radial cross-sectional hemolysis indices of three structures where the blade deflection angle of the impeller is 90°, 110° and 180° respectively according to some embodiments of the present disclosure. FIG. 27 is another comparison diagram of radial cross-sectional flow fields of three structures where the blade deflection angle of the impeller is 90°, 110° and 180° respectively according to some embodiments of the present disclosure. FIG. 28 is another comparison diagram of radial cross-sectional pressure of three structures where the blade deflection angle of the impeller is 90°, 110° and 180° respectively according to some embodiments of the present disclosure. FIG. 29 is another comparison diagram of radial cross-sectional vorticity of three structures where the blade deflection angle of the impeller is 90°, 110° and 180° respectively according to some embodiments of the present disclosure. FIG. 30 is another comparison diagram of radial cross-sectional scalar shear stress of three structures where the blade deflection angle of the impeller is 90°, 110° and 180° respectively according to some embodiments of the present disclosure. FIG. 31 is another comparison diagram of radial cross-sectional hemolysis indices of three structures where the blade deflection angle of the impeller is 90°, 110° and 180° respectively according to some embodiments of the present disclosure.

Three impeller structures with the blade deflection angle θ of 90°, 110° and 180° are selected for simulation experiments to realize the comparison of hydraulic performance and the hemolytic performance achieved by the three impeller structures. The results are shown in FIG. 18-FIG. 31. The three impeller models used in the simulation experiments all have two uniformly distributed blades 2.

It can be seen from FIG. 18 that in the structure with the blade deflection angle θ of 110°, the pressure difference between the impeller inlet and the impeller outlet is the highest. Correspondingly, the impeller can achieve a larger head under this structure. The structure with the blade deflection angle θ of 90° is the second, while the structure with the blade deflection angle θ of 180° produces a negative pressure difference. Therefore, compared with the two structures with the blade deflection angle θ of 90° and 180°, the impeller with the blade deflection angle θ of 110° may achieve better hydraulic performance.

It can be seen from FIG. 19 that in the structure with the blade deflection angle θ of 110°, the average scalar shear stress generated by the impeller during rotation is significantly lower. The structure with the blade deflection angle θ of 180° is the second, and the structure with the blade deflection angle θ of 90° produces the highest average scalar shear stress. The effect of lower average scalar shear stress is also reflected in FIG. 20. It can be seen that in the structure with the blade deflection angle θ of 110°, the hemolysis index is lower than that of the other two structures, indicating that the impeller under this structure may ensure that the pumped blood has good physiological indicators. In the structure with the blade deflection angle θ of 180°, the hemolysis index was slightly higher than that of the structure with the blade deflection angle θ of 110°, and the two structures were almost equal. In the structure with the blade deflection angle θ of 90°, the hemolysis index increased significantly.

On the basis of the above data, the difference between the hydraulic performance and the hemolytic performance of the three impellers may be more intuitively displayed through FIG. 21-FIG. 31 when the blade deflection angle θ is 90°, 110° and 180°.

FIG. 21 is a comparison diagram of three-dimensional flow fields of three impeller structures. Arrows with different color depths in the drawing represent the velocity values of fluid when the fluid flows through the impeller. It can be seen that the blood (i.e., the blood) is in the same state before entering the impeller inlet. In the structure with the blade deflection angle θ of 110°, the blood flow rate changes more smoothly and evenly in the process of flowing through the impeller. In the structure with the blade deflection angle θ of 90°, the flow velocity of the blood at the inlet side of the blade 2 may suddenly increase, and at the same time, more turbulent flow may be generated when the blood flows through the impeller. In the structure with the blade deflection angle θ of 180°, the flow velocity of the blood at the outlet side of the blade 2 may suddenly decrease, and at the same time, the blood also produces turbulent flow in the process of flowing through the impeller, which is better than that of the structure with the blade deflection angle θ of 90°.

FIG. 22 shows the comparison diagram of radial cross-sectional flow fields of the three impeller structures, and the velocity values of the blood flowing through the impeller are also represented by arrows of different colors. In the structure with the blade deflection angle θ of 110°, when the blood flows through the impeller, the flow velocity changes more smoothly and evenly, and the structure has better hydraulic performance than the other two structures.

FIG. 23 shows the comparison diagram of radial cross-sectional pressure of three impeller structures. Different colors are used in the drawing to represent the pressure distribution of blood flowing through the impeller. It can be seen that in the structure with the blade deflection angle θ of 110°, there is a more obvious pressure difference between the impeller inlet and the impeller outlet. Compared with the other two structures, the impeller with the blade deflection angle θ of 110° has better hydraulic performance.

FIG. 24 shows the comparison diagram of radial cross-sectional vorticity of three impeller structures, and different colors are used in the drawing to represent the distribution of the vorticity of the blood flowing through the impeller. It can be seen that in the structure with the blade deflection angle θ of 110°, the vorticity generated by the blood flowing through the impeller is the least, and the distribution is relatively uniform, which avoids the concentration of vortices, and makes the blood flow more smoothly through the impeller and helps to reduce flow loss. In the structure with the blade deflection angle θ of 180°, the vorticity generated by the blood is the second, while the vorticity generated by the blood is the most in the structure with the blade deflection angle θ of 90°. Compared with the other two structures, the impeller with the blade deflection angle θ of 110° has better hydraulic performance.

FIG. 25 shows the comparison diagram of radial cross-sectional scalar shear stress of three impeller structures, and the distribution of the scalar shear stress is shown by using different colors of blood flowing through the impeller. It can be seen that in the structure with the blade deflection angle θ of 110°, the scalar shear stress of the blood flowing through the impeller is the least, especially at the impeller outlet. In the structure with the blade deflection angle θ of 180°, the blood receives more scalar shear stress, while in the structure with the blade deflection angle θ of 90°, the blood receives the most scalar shear stress.

FIG. 26 shows the comparison diagram of the radial cross-sectional hemolysis indices of three impeller structures, and different colors are used in the drawing to represent the distribution of the hemolysis indices of the fluid flowing through the impeller. Corresponding to the scalar shear stress, in the structure with the blade deflection angle θ of 110°, the hemolysis index of blood flowing through the impeller and after exiting the impeller is the lowest compared with the other two structures. In the structure with the blade deflection angle θ of 180°, the hemolysis index is higher than that of the structure with the blade deflection angle θ of 110°, and the hemolysis index is the highest in the structure with the blade deflection angle θ of 90°. Compared with the other two structures, the impeller with the blade deflection angle θ of 110° has better hemolysis performance.

FIG. 27-FIG. 31 select another radial section of the impeller to carry out the simulation experiments carried out in FIG. 22-FIG. 26 to further corroborate the hydraulic performance and the hemolytic performance achieved by the impeller under the above three structures with the blade deflection angle θ of 90°, 110° and 180°. The experimental effects shown in FIG. 27-FIG. 31 are the same as those shown in FIG. 22-FIG. 26, and will not be repeated here.

It can be seen from the above simulation experiments that, compared with the structures with the blade deflection angle θ of 90° and 180°, the impeller with the blade deflection angle θ of 110° may achieve higher hydraulic performance and reduce the hemolysis of the pumped blood.

As shown in FIG. 3, in some embodiments, when the impeller is projected along the axial direction of the hub 1, a radial inclined angle between the inlet edge line 212 and the start point of the profile line 214 is a tangential forward sweep angle β, and the angle of the tangential forward sweep angle β is 2°-8°.

In some embodiments, the angle of the tangential forward sweep angle β comprises, but is not limited to, 2°, 3°, 4°, 5°, 6°, 7°, or 8°.

In some embodiments, when the blood enters the impeller inlet, the tangential forward sweep angle β may make the tangential velocity $V_t$ generate a component velocity $V_1$ towards the central axis of the hub 1. The component velocity $V_1$ may make the blood gather to the hub 1 during the rotational flow from the impeller inlet to the impeller outlet, thereby reducing the shear stress on the blood, avoiding the generation of secondary flow, and making the blood flow more stable. The secondary flow refers to a deviation of the blood along the radial direction of the hub 1 due to the action of lateral force (i.e., the radial force of the hub 1) during the process of blood flow. The secondary flow is medium flow superimposed on a main flow (the flow of blood along the axial direction of the hub 1). In addition to the lateral force, a separation flow, a vortex, etc., may also cause corresponding secondary flow.

In some embodiments, since the blade 2 has the structure with the tangential forward sweep angle β, the blood generates the component velocity $V_1$ towards the central axis of the hub 1 during the process of flowing through the impeller, and the component velocity $V_1$ may produce a certain gather of blood. As a result, the blood keeps flowing around the circumference of the hub 1 to form a stable flow field. The secondary flow of blood under the influence of the lateral force or the separation flow may be effectively avoided, which helps to reduce the flow loss of blood, improve the hydraulic performance of the impeller, and also reduce the blood damage, and thus the impeller has better hemolysis performance.

As shown in FIG. 2, in some embodiments, when the impeller is projected along the radial direction of the hub 1, the inclined angle between the inlet edge line 212 and the horizontal line is an axial forward sweep angle $\gamma$, and the angle of the axial forward sweep angle $\gamma$ is 100-26°.

In some embodiments, the angle of the axial forward sweep angle $\gamma$ comprises, but is not limited to, 10°, 11°, 12°, 13°, 14°, 15°, 16°, 17°, 18°, 19°, 20°, 21°, 22°, 23°, 24°, 25° or 26°.

In some embodiments, when blood enters the impeller inlet, the axial forward sweep angle $\gamma$ may make the axial velocity $V_a$ generate a component velocity $V_2$ towards the central axis of the hub 1. The component velocity $V_2$ may make the blood gather to the hub 1 during the rotational flow from the impeller inlet to the impeller outlet, thereby reducing the shear stress on the blood, avoiding the generation of secondary flow, and making the blood flow more stable.

In some embodiments, since the blade 2 has the structure with the axial forward swept angle $\gamma$, the blood generates the component velocity $V_2$ towards the central axis of the hub 1 during the process of flowing through the impeller. This component velocity $V_2$ and the component velocity $V_1$ generated by the structure with the tangential forward sweep angle $\beta$ work together to produce a certain gather effect on the blood, so that the blood may keep flowing in the circumference of the hub 1 to form a stable flow field. The secondary flow of blood under the influence of the lateral force or the separation flow may be effectively avoided, which helps to reduce the flow loss of blood, improve the hydraulic performance of the impeller, and also reduce the blood damage, and thus the impeller has better hemolysis performance.

In some embodiments, in the same radial section of the impeller, the ratio of the outer diameter of the blade 2 to the outer diameter of the hub 1 is 1.25-3.25.

In some embodiments, the outer diameter of the hub 1 gradually increases from the inlet end 11 to the outlet end 12, while the outer diameter of the blade 2 remains unchanged. Therefore, the ratio of the outer diameter of the blade 2 to the outer diameter of the hub 1 gradually decreases from the start point of the profile line 214 to the end point of the profile line 215.

In some embodiments, the ratio of the length of the blade 2 to the length of the hub 1 is 0.86-0.87 along the axial direction of the hub 1, and the end point of the profile line 215 is close to the outlet end 12.

In some embodiments, the installation angle of the outer edge profile line 211 is different from the installation angle of the hub profile line 216 at the same axial location, which makes the blade 2 a twisted blade. The twisted blade helps the blood to fit the impeller, increase the hydraulic performance that the impeller may achieve, and reduce the generation of special flow structure.

In some embodiments, the impeller may have the standard parameters of the impeller and the adjustment parameters of the impeller. The standard parameters of the impeller may refer to general parameters of a standard impeller product, such as default factory parameters of the product, etc. The standard parameters of the impeller may comprise a plurality of sets of parameters, and each set of parameters may correspond to an impeller product. The adjustment parameters of the impeller are parameters used to adjust the standard parameters of the impeller.

In some embodiments, the adjustment parameters of the impeller may comprise a first impeller adjustment parameter (also referred to as first adjustment parameter of the impeller) and a second impeller adjustment parameter. The first impeller adjustment parameter may be determined based on the standard parameters of the impeller and customization requirements, and the first impeller adjustment parameter may be used for preliminary adjustment of the impeller parameters, for example, determining an approximate shape of the impeller. The second impeller adjustment parameter may be determined based on the first impeller adjustment parameter and patient information, and the second impeller adjustment parameter may be used to further finely adjust the impeller on the basis of the adjustment of the first impeller adjustment parameter.

The customization requirements are customization requirements put forward by different patients based on different requirements for products. For example, different patients may have different performance requirements for the products. In some embodiments, the customization requirements may comprise one or more of a hydraulic performance requirement, a blood pumping performance requirement, and a hemolytic performance requirement. The hydraulic performance requirement comprises a requirement for an output flow, a requirement for the pressure difference between the inlet end and the outlet end of the catheter pump, etc. The blood pumping performance requirement comprises a requirement for a pressure value of human blood circulation, etc. The hemolytic performance requirement comprises a requirement for the shear stress of the blood during the pumping process, a requirement for the smoothness of the blood flow, etc.

In some embodiments, the first impeller adjustment parameter may comprise a first adjustment parameter, and may also comprise a first adjustment function of the outer edge profile line. The first adjustment parameter comprises the inlet inclined angle $\alpha$, the inlet installation angle $a_m$, the blade deflection angle $\theta$, the tangential forward sweep angle $\beta$, the axial forward sweep angle $\gamma$, etc. The first adjustment function comprises a curve formula obtained by adjusting the outer edge profile line of the standard product.

The patient information may refer to information related to the patient's own condition, and different impeller parameters may be customized according to the different conditions of different patients. In some embodiments, the patient information may comprise one or more of the patient's basic information, implantation location, and blood vessel diameter. The basic information may comprise the age of the patient, etc. Since the standard products are usually customized for adults, and some scaling may be required for children. The implantation location comprises a specific location where the device is implanted, e.g., a left ventricle or a right ventricle, etc. The blood vessel diameter comprises an actual diameter of the patient's blood vessel at the site of implantation to more specifically define the outer diameter of the impeller.

In some embodiments, the second impeller adjustment parameter may comprise one or more of an outer blade diameter, a second adjustment parameter, and a second adjustment function of the outer edge profile line. The second adjustment parameter may comprise the inlet inclined angle α, the inlet installation angle $a_m$, the blade deflection angle θ, the tangential forward sweep angle β, the axial forward sweep angle γ, etc., which are further finely adjusted on the basis of the first adjustment. The adjustment function comprises a curve formula obtained by further fine adjustment on the basis of the outer edge profile line of the first adjustment function.

In some embodiments, various feasible ways may be used to obtain parameters for adjusting the impeller based on different requirements of different patients, and adjust the impeller accordingly. In some embodiments, the parameters for impeller adjustment may be determined based on a parameter adjustment model. In some embodiments, the parameter adjustment model may be a machine learning model.

Figure 32:
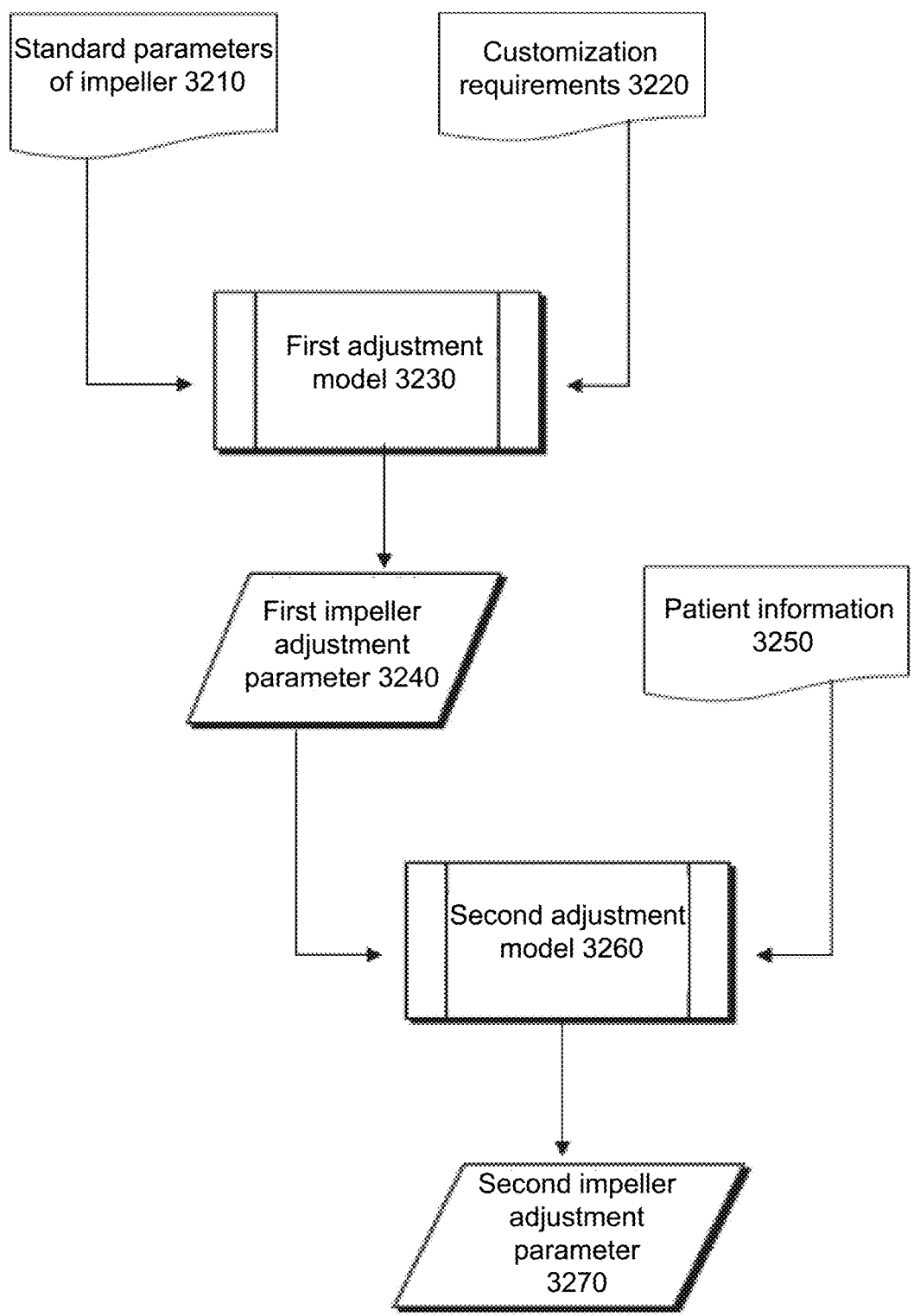
FIG. 32 is a schematic diagram of a parameter adjustment model according to some embodiments of the present disclosure.

FIG. 32 is a schematic diagram of the parameter adjustment model according to some embodiments of the present disclosure.

In some embodiments, as shown in FIG. 32, the parameter adjustment model may comprise a first adjustment model 3230 and a second adjustment model 3260. In some embodiments, the first adjustment model 3230 and the second adjustment model 3260 may be models obtained from a convolutional neural network or a deep neural network or a combination thereof, or the like.

In some embodiments, an input of the first adjustment model 3230 may comprise the standard parameters of the impeller 3210 and the customization requirements 3220, and an output of the first adjustment model 3230 may comprise the first impeller adjustment parameter 3240.

In some embodiments, an input of the second adjustment model 3260 may comprise the first impeller adjustment parameter 3240 and the patient information 3250, and an output of the second adjustment model 3260 may comprise the second impeller adjustment parameter. The first impeller adjustment parameter 3240 may be the first impeller adjustment parameter 3240 outputted based on the first adjustment model 3230.

In some embodiments, the trained first adjustment model 3230 and the second adjustment model 3260 are obtained based on a large amount of extensive data, e.g., historical data of the patient, simulation data, etc., and the adjustment parameters of the impeller are preliminarily determined and further finely determined respectively based on the first adjustment model 3230 and the second adjustment model 3260, and the data is reliable and efficient.

In some embodiments, the first adjustment model 3230 and the second adjustment model 3260 may be obtained through separate training or joint training.

For example, the first adjustment model 3230 and the second adjustment model 3260 may be obtained separately through separate training.

Training samples with training labels may be inputted into an initial first adjustment model, the training samples may comprise a plurality of sets of historical patient customization requirements, and the corresponding training labels may be parameters of simulation. The parameters of the initial first adjustment model are updated through training iterations until preset conditions are met, and the trained first adjustment model is obtained. In some embodiments, the method of iteratively updating the model parameters may comprise a conventional model training method such as stochastic gradient descent.

The training samples with the training labels may be inputted into an initial second adjustment model. The training samples may comprise a plurality of sets of historical patient customization conditions and corresponding simulation parameters thereof. The corresponding training labels may be the parameters of the actual impeller customized based on expert experience. The parameters of the initial second adjustment model are updated through training iterations until the preset conditions are met, and the trained second adjustment model is obtained. In some embodiments, the method of iteratively updating the model parameters may comprise the conventional model training method such as stochastic gradient descent.

For another example, the first adjustment model 3230 and the second adjustment model 3260 may be obtained through joint training. The output of the first adjustment model 3230 may be used as the input of the second adjustment model 3260.

The sample data jointly trained by the first adjustment model 3230 and the second adjustment model 3260 may comprise a plurality of sets of historical patient customization records (including the customization requirements and the patient information), labeled as the parameters of the actual impeller customized based on expert experience. A loss function is constructed based on the output of the initial first adjustment model and the initial second adjustment model, and the parameters of the first adjustment model and the second adjustment model are updated synchronously. By updating the parameters until the loss function satisfies the preset conditions, the trained first adjustment model and the second adjustment model are obtained. The preset conditions may be that the loss function is less than the threshold, converges, or the training period reaches the threshold.

In some embodiments, the impeller may be used in the ventricular assist device. The working principle of the ventricular assist device is that the catheter of the ventricular assist device is sent to the left ventricle through the femoral artery route, an inflow port of the catheter is located in a left ventricular outflow tract, and an outflow port of the catheter is located in the aorta. When the ventricular assist device is working, the rotating impeller may suck the blood from the inflow port of the catheter of the left ventricle into the catheter, and then return the blood to the aorta through the outflow port of catheter of the aorta, which achieves the effect of cardiac assistance.

In some embodiments, a ventricular assist device may include a catheter and an impeller as in any of the preceding embodiments disposed in the catheter. The ventricular assist device may rely on the impeller of any of the foregoing embodiments to realize the pumping of blood, and has the beneficial effects of the corresponding impeller embodiment, which will not be repeated here.

The basic concepts have been described above. Obviously, for technicians skilled in the art, the above detailed disclosure is merely an example, and does not constitute a limitation of the present disclosure. Although not explicitly described herein, various modifications, improvements, and corrections to this disclosure may occur to technicians skilled in the art. Such modifications, improvements, and corrections are suggested in this disclosure, so such modifications, improvements, and corrections still belong to the spirit and scope of the exemplary embodiments of this disclosure.

Meanwhile, the present disclosure uses specific words to describe the embodiments of the present disclosure. Such as "one embodiment," "an embodiment," and/or "some embodiments" means a certain feature, structure, or characteristic associated with at least one embodiment of this disclosure. Therefore, it should be emphasized and noted that two or more references to "an embodiment" or "one embodiment" or "an alternative embodiment" in various places in this disclosure are not necessarily referring to the same embodiment. Furthermore, certain features, structures or characteristics of the one or more embodiments of this disclosure may be combined as appropriate.

Furthermore, unless explicitly stated in the claims, the order of processing elements and sequences described in this disclosure, the use of alphanumerics, or the use of other names is not intended to limit the order of the processes and methods of this disclosure. While the foregoing disclosure discusses, by way of various examples, some embodiments presently believed to be useful, it is to be understood that such details are for purposes of illustration only and that the appended claims are not limited to the disclosed embodiments, on the contrary, the claims are intended to cover all modifications and equivalent combinations that fall within the spirit and scope of the embodiments of this disclosure. For example, although the system components described above may be implemented by hardware devices, they may also be implemented by software-only solutions, such as installing the described systems on existing servers or mobile devices.

Similarly, it should be noted that, in order to simplify the expressions disclosed in this specification and then help the understanding of one or more embodiments, in the foregoing description of the embodiments of this disclosure, various features may sometimes be combined into one embodiment, accompanying drawing or description. However, this method of disclosure does not imply that the subject matter of the description requires more features than are recited in the claims. Rather, the claimed subject matter may lie in less than all features of a single foregoing disclosed embodiment.

Some examples use numbers to describe quantities of ingredients and attributes, it should be understood that such numbers used to describe the examples, in some examples, use the modifiers "about", "approximately" or "substantially" to retouch. Unless stated otherwise, "about", "approximately" or "substantially" means that a variation of ±20% is allowed for the stated number. Accordingly, in some embodiments, the numerical parameters set forth in the disclosure and claims are approximations that may vary depending upon the desired characteristics of individual embodiments. In some embodiments, the numerical parameters should take into account the specified significant digits and use a general digit reservation method. Notwithstanding that the numerical fields and parameters used in some embodiments of this disclosure to confirm the breadth of their ranges are approximations, in specific embodiments such numerical values are set as precisely as practicable.

For each patent, patent application, patent application publication, and other material, such as an article, a book, a specification, a publication, a document, etc., cited in this disclosure, the entire contents of which are hereby incorporated into this disclosure by reference. History application documents that are inconsistent with or conflict with the contents of this disclosure are excluded, as are documents (currently or hereafter appended to this disclosure) limiting the broadest scope of the claims of this disclosure. It should be noted that, if there is any inconsistency or conflict between the descriptions, definitions and/or use of terms in the accompanying materials of this disclosure and the contents of this specification, the descriptions, definitions and/or use of terms in this disclosure shall prevail.

Finally, it should be understood that the embodiments described in this disclosure are only used to illustrate the principles of the embodiments of this disclosure. Other variations are also possible within the scope of this disclosure. Therefore, by way of example and not limitation, alternative configurations of the embodiments of this disclosure may be considered consistent with the instructions of this disclosure. Accordingly, the embodiments of this disclosure are not limited to the embodiments expressly introduced and described in this disclosure.

What is claimed is:

1. An impeller, comprising a hub and at least one blade fixed on an outer periphery of the hub;
   the hub comprises an inlet end and an outlet end;
   the blade comprises an action surface, a contour line of the action surface comprises an outer edge profile line away from the hub, an endpoint of the outer edge profile line close to the inlet end is a start point of the profile line, and an endpoint of the outer edge profile line close to the outlet end is an end point of the profile line;
   the outer edge profile line is a smooth space curve, and a curvature of the outer edge profile line along an axial direction of the hub gradually decreases from the start point of the profile line to the end point of the profile line;
   wherein an inclined angle between a tangent line at the start point of the profile line and a tangential velocity at the start point of the profile line is an inlet inclined angle of the outer edge profile line;
   a resultant velocity of an axial velocity at the start point of the profile line and the tangential velocity at the start point of the profile line is a relative velocity at the start point of the profile line, and an inclined angle between the relative velocity at the start point of the profile line and the tangential velocity at the start point of the profile line is an inlet installation angle of the outer edge profile line;
   the inlet inclined angle is greater than the inlet installation angle.

2. The impeller of claim 1, wherein a curvature change rate of the outer edge profile line along the axial direction of the hub gradually decreases from the start point of the profile line to the end point of the profile line.

3. The impeller of claim 1, wherein a difference between the inlet inclined angle and the inlet installation angle is less than or equal to 5°.

4. The impeller of claim 1, wherein:
   a calculation formula of the inlet installation angle is as follows:

$$a_m = \arctan \frac{V_a}{V_t};$$

where, $a_m$ is the inlet installation angle, $V_a$ is the axial velocity at the start point of the profile line, and $V_t$ is the tangential velocity at the start point of the profile line;
the calculation formula of the axial velocity at the start point of the profile line is as follows:

$$V_a = \frac{Q}{A} = \frac{4Q}{\pi D^2};$$

where, Q is a preset flow rate, A is a cross-sectional area of a catheter hole for installing the impeller, and D is an inner diameter of the catheter;
the calculation formula of the tangential velocity at the start point of the profile line is as follows:

$$V_t = \omega \frac{D}{2};$$

where, ω is a preset rotational velocity of the blade.

5. The impeller of claim 1, wherein the inlet inclined angle is 25°-35°.

6. The impeller of claim 1, wherein the outer edge profile line is a spiral curve with Gaussian curvature gradient, and the formula is as follows:

$$x = 0.7 + 1.2 * \sin\left(\pi \frac{z + 2.14}{5}\right)$$

$$y = 1.85 - 3.7 e^{-0.5\left(\frac{z-1.3}{1.3}\right)^2}.$$

7. The impeller of claim 1, wherein an inclined angle between an axial plane where the start point of the profile line is located and an axial plane where the end point of the profile line is located is a blade deflection angle, and the angle of the blade deflection angle is 90°-150°.

8. The impeller of claim 1, wherein the contour line of the action surface further comprises an inlet edge line intersecting with the start point of the profile line;
when the impeller is projected along an axial direction of the hub, an inclined angle between the inlet edge line and the axial direction of the start point of the profile line is a tangential forward sweep angle, and the tangential forward sweep angle is 2°-8°.

9. The impeller of claim 1, wherein the contour line of the action surface further comprises an inlet edge line intersecting with the start point of the profile line;
when the impeller is projected along a radial direction of the hub, an included angle between the inlet edge line and a horizontal line is an axial forward sweep angle, and the axial forward sweep angle is 10°-26°.

10. The impeller of claim 1, wherein in the same radial section of the impeller, a ratio of an outer diameter of the blade to an outer diameter of the hub is 1.25-3.25.

11. The impeller of claim 1, wherein a ratio of a length of the blade to a length of the hub is 0.86-0.87 along the axial direction of the hub.

12. The impeller of claim 1, wherein the impeller has standard parameters and adjustment parameters, and the adjustment parameters of the impeller are parameters used to adjust the standard parameters of the impeller.

13. The impeller of claim 12, wherein the adjustment parameters of the impeller comprise a first adjustment parameter of the impeller and a second adjustment parameter of the impeller, the first adjustment parameter of the impeller being determined based on the standard parameters of the impeller and customization requirements, and the second adjustment parameter of the impeller being determined based on the first adjustment parameter of the impeller and patient information.

14. The impeller of claim 13, wherein the customization requirements comprise one or more of a hydraulic performance requirement, a blood pumping performance requirement and a hemolytic performance requirement.

15. The impeller of claim 13, wherein the first adjustment parameter of the impeller comprises a first adjustment parameter and/or a first adjustment function of the outer edge profile line.

16. The impeller of claim 13, wherein the patient information comprises one or more of basic information, an implantation position and a blood vessel diameter of a patient.

17. The impeller of claim 13, wherein the second adjustment parameter of the impeller comprises one or more of an outer diameter of the blade, a second adjustment parameter and a second adjustment function of the outer edge profile line.

18. A ventricular assist device, comprising: a catheter and the impeller according to claim 1 arranged in the catheter.

* * * * *